United States Patent
Pinchasik

(10) Patent No.: US 6,821,293 B2
(45) Date of Patent: Nov. 23, 2004

(54) MANDREL AND METHOD FOR MAKING STENTS

(75) Inventor: Gregory Pinchasik, Herzeliya (IL)

(73) Assignee: Medinol Ltd., Tel Aviv (IL)

( * ) Notice: Subject to any disclaimer, the term of this patent is extended or adjusted under 35 U.S.C. 154(b) by 8 days.

(21) Appl. No.: 10/280,729

(22) Filed: Oct. 25, 2002

(65) Prior Publication Data

US 2004/0079737 A1 Apr. 29, 2004

(51) Int. Cl.[7] .............................. A61F 2/06; B23K 26/20; B23K 31/02
(52) U.S. Cl. ...................... 623/1.15; 156/180; 156/433; 228/173.5; 219/121.63; 219/121.64
(58) Field of Search .............................. 623/1.15, 1.16; 219/121.63, 121.64

(56) References Cited

U.S. PATENT DOCUMENTS

| | | | | |
|---|---|---|---|---|
| 5,039,218 A | * | 8/1991 | Chesler et al. | ............. 356/73.1 |
| 5,824,043 A | * | 10/1998 | Cottone, Jr. | ................ 623/1.13 |
| 5,906,759 A | | 5/1999 | Richter | ................... 219/121.63 |
| 6,056,187 A | * | 5/2000 | Acciai et al. | ............ 228/173.5 |
| 6,136,023 A | * | 10/2000 | Boyle | ......................... 623/1.22 |
| 6,514,063 B2 | * | 2/2003 | Acciai et al. | ............... 425/116 |
| 2002/0038767 A1 | * | 4/2002 | Trozera | ...................... 205/667 |
| 2003/0187498 A1 | * | 10/2003 | Bishop | ...................... 623/1.16 |

* cited by examiner

Primary Examiner—Geoffrey S. Evans
(74) Attorney, Agent, or Firm—Kenyon & Kenyon

(57) ABSTRACT

A patterned sheet having two long sides is wrapped around a mandrel. The mandrel is provided with at least one flat surface. The long sides of the sheet are secured adjacent to the flat surface of the mandrel and points along the long sides of the sheet are connected by laser welding or other connecting means. The laser beam is directed substantially perpendicular to the welding plane of the points to be welded, even if the weld points do not all lie on a single line parallel to the mandrel's longitudinal axis.

65 Claims, 18 Drawing Sheets

MANDREL AND METHOD FOR MAKING STENTS

FIELD OF THE INVENTION

The present invention relates generally to an apparatus and method for fabricating stents by deforming patterned sheets into substantially tubular shapes and connecting the edges of the sheet. More specifically, the invention is especially directed to an apparatus and method that is especially applicable to making stents having weld point pairs that are not disposed along a single weld line when the sheet is rolled into a substantially tubular shape.

BACKGROUND

Stents are known in the art. They are typically formed of a cylindrical metal mesh which can expand when pressure is internally applied. Alternatively, they can be formed of wire formed into a cylindrical shape.

U.S. Pat. No. 5,906,759, which is hereby incorporated herein by reference in its entirety, provides a stent fabrication method which can produce stents with intricate and delicate designs. In particular, the stent fabrication methods and apparatus described at columns 10–26 of that patent (and the accompanying figures) may be advantageously used along with the present invention. The method disclosed in the '759 patent involves first creating a version, preferably flat, of the desired stent pattern from a piece of thin material, e.g., sheet metal. The flat pattern can be produced through a variety of suitable techniques that are well known to those skilled in the art. Once the flat pattern has been formed, it is deformed so as to cause its edges to meet.

To create a cylindrical stent from a flat metal pattern, the flat metal is rolled or wrapped around a mandrel until the edges meet. The locations where the edges meet are joined together, such as by laser welding. Afterwards, the stent may be finished in a variety of well known ways, e.g., polishing, either mechanically or electrochemically, plating, or applying a medicament or some other coating.

In making stents for specific applications it may be desirable to utilize sheets which, when rolled into a tube, have weld points that are not disposed along a single weld line disposed along the longitudinal axis of the mandrel. Instead, for example, the weld points may be disposed on one or more weld lines that are disposed laterally to the longitudinal axis of the mandrel. If a mandrel having a substantially circular cross-section is used, the greater the distance that the weld points are displaced laterally from the longitudinal axis of the mandrel, the more acute will be the angle that the laser beam makes with the weld points.

Accordingly, it is an object of the invention to remove the drawbacks of the prior art and to provide an apparatus and method which allows for the making of stents utilizing sheets which when rolled into a tubular shape have weld points that are not disposed only along a single weld line, while still allowing the laser beam to intersect the weld points at an angle that is substantially perpendicular.

SUMMARY OF THE INVENTION

In accordance with an exemplary embodiment of the present invention, it is an object of this invention to provide a mandrel for forming a stent, comprising: a member having a first end, a second end and an external surface with the external surface provided with at least one substantially flat surface extending between the first end and the second end.

It is another object of this invention to provide a mandrel for forming a stent comprising: a longitudinal member having a first end and second end. The longitudinal member has a substantially triangular cross-sectional shape, wherein each of the three sides defining the substantially triangular shape is a substantially flat surface that extends between the first end and the second end of the mandrel.

It is yet another object of this invention to provide an apparatus comprising a mandrel having an axis, and having a substantially flat surface. A means is provided to wrap a flat sheet provided with a stent pattern around the mandrel so that the edges of the sheet meet on or near the substantially flat surface of the mandrel. A means for joining the edges together may be disposed adjacent to the mandrel to provide, for example, energy such as a laser beam directed at an angle substantially perpendicular to the flat surface. Alternatively or additionally, the means for joining may also provide an adhesive, such as glue. The means for joining may be supported for movements in directions parallel to and orthogonal to the axis of the mandrel to permit joining at points which are laterally displaced from each other on the flat surface.

It is still another object of this invention to provide and apparatus for fabricating a stent, comprising: a platform adapted to receive a sheet of material to be formed into the stent. The sheet has a longitudinal axis, a first major surface, a second major surface, a first long side, and a second long side. The first long side is provided with a plurality of weld points and the second long side is provided with a plurality of corresponding weld points. The weld points are disposed so that when the sheet is formed into a substantially tubular shape, the weld points on the first long side are adjacent to the corresponding weld points on the second long side to form a plurality of weld point pairs. A mandrel having an external surface and a first end and a second end defining a longitudinal axis is provided. The mandrel is sized to have an external perimeter about the longitudinal axis that is substantially equal to or less than the unexpanded internal perimeter of the stent to be fabricated. The external surface of the mandrel is provided with at least one substantially flat surface extending between the first end and the second end. A means is provided for deforming the sheet against the external surface of the mandrel so that the sheet is deformed into a substantially tubular shape. A means for aligning and securing is provided for aligning and securing the weld points on the first long side and the corresponding weld points on the second long side to form a plurality of weld point pairs so that they can be connected, e.g., by welding. A means for joining, for example, a laser, may be provided for joining the weld points on the first long side to the corresponding weld points on the second long side. The means for deforming and the means for aligning and securing are adapted to secure the aligned weld points adjacent to the substantially flat surface of the mandrel so that each of the aligned weld points comprising each of the weld point pairs lies in a plane that is substantially perpendicular to the laser beam.

It is a further object of this invention to provide an apparatus for fabricating a stent, comprising: a platform adapted to receive a sheet of material to be formed into the stent. The sheet of material has a longitudinal axis, a first major surface, a second major surface, a first long side, and a second long side with the first and second long sides substantially parallel to the longitudinal axis of the sheet. The first long side may be provided with a plurality of first weld line weld points and a plurality of second weld line weld points and the second long side may be provided with a plurality of first weld line weld points and a plurality of second weld line weld points. The weld points are disposed so that when the sheet is formed into a substantially tubular shape the first weld line weld points on the first long side are adjacent to the corresponding first weld line weld points on the second long side to form a plurality of first weld line weld point pairs disposed on a first weld line having a longitudinal axis substantially parallel to the longitudinal axis of the sheet. The weld points are also disposed so that when the stent is formed into a substantially tubular shape the second weld line weld points on the first long side are adjacent to the corresponding second weld line weld points on the second long side to form a plurality of second weld line weld points disposed on a second weld line having a longitudinal axis that is substantially parallel to the longitudinal axis of the sheet. Of course, the weld points on the first long side and the second long side need not actually be disposed on lines at all; they need only meet in weld point pairs when the sheet is rolled and the first and second long sides meet each other. A mandrel having an external surface and a first end and a second end defining a longitudinal axis is provided. The mandrel is sized to have an external perimeter about the longitudinal axis that is substantially equal to or less than the internal perimeter of the stent to be fabricated. The external surface of the mandrel is provided with at least one substantially flat surface extending between the first end and the second end. A means is provided for deforming the sheet against the external surface of the mandrel so that the sheet is deformed into a substantially tubular shape. The means for deforming is adapted so that the first long side and the second long side remain substantially parallel to each other when the sheet is deformed into the tubular shape. A means is provided for aligning and securing the weld points on the first long side to the corresponding weld points on the second long side so that the weld points form weld point pairs that can be connected. A means for joining, for example, a laser, may be provided for securing the aligned weld points. The means for deforming and the means for aligning and securing are adapted to secure the aligned weld points adjacent to the substantially flat surface of the mandrel so that the aligned weld points lie in a plane that is substantially parallel to the substantially flat surface of the mandrel and substantially perpendicular to the laser beam.

It is a still further object of this invention to provide a method of making a stent comprising: wrapping a sheet provided with a stent pattern and having two opposed sides about a mandrel having an axis, and having a flat surface, so as to cause the two opposing sides to meet on the flat surface. A means for joining is utilized for joining the two opposing sides at two or more points not disposed along a single line parallel to the longitudinal axis of the mandrel. The means for joining is directed substantially perpendicular to the flat surface.

It is a yet further object of this invention to provide a method of making a stent, comprising the steps of: utilizing a sheet of material to be formed into the stent, the sheet having a longitudinal axis, a first major surface, a second major surface, a first long side, and a second long side. The first long side is provided with a plurality of weld points and the second long side is provided with a plurality of corresponding weld points. The weld points are disposed so that when the stent is formed into a substantially tubular shape, the weld points on the first long side are adjacent to the corresponding weld points on the second long side to form a plurality of weld point pairs that need not be disposed on only a single weld line. The sheet is deformed against the external surface of a mandrel so that the sheet is deformed into a substantially tubular shape. The mandrel has an external surface and a first end and a second end defining a longitudinal axis. The mandrel is sized to have an external perimeter substantially equal to or less than the internal perimeter of the stent to be fabricated. The external surface of the mandrel is provided with at least one substantially flat surface extending between the first end and the second end. Each of the plurality of weld points is aligned and secured adjacent to the substantially flat surface of the mandrel so that the weld points lie in a plane that is substantially parallel to the substantially flat surface of the mandrel, and so that the weld points on the first long side are adjacent to the corresponding weld points on the second long side to form a plurality of weld point pairs. The corresponding weld points may be connected by utilizing a means for joining, e.g., a laser beam, that is directed substantially perpendicular to the plane in which the weld points lie.

It is another object of this invention to provide a method of making a stent, comprising the steps of: utilizing a sheet of material to be formed into the stent, the sheet having a longitudinal axis, a first major surface, a second major surface, a first long side, and a second long side with the first and second long sides substantially parallel to the longitudinal axis of the sheet. The first long side is provided with a plurality of weld points and the second long side is provided with a plurality of weld points. The weld points are disposed so that when the sheet is formed into a substantially tubular shape, the weld points on the first long side are adjacent to the corresponding weld points on the second long side to form a plurality of weld point pairs. The weld points may be disposed so that the weld point pairs are not all disposed on a single line parallel to the mandrel's longitudinal axis when the sheet is formed into a substantially tubular shape. The sheet is deformed against the external surface of a mandrel so that the sheet is deformed into a substantially tubular shape. The mandrel has an external surface and a first end and a second end defining a longitudinal axis. The mandrel is sized to have an external perimeter that is substantially equal to or less than the internal perimeter of the stent to be fabricated. The external surface of the mandrel is provided with at least one substantially flat surface extending between the first end and the second end. The first and second weld points are aligned and are secured adjacent to the substantially flat surface of the mandrel so that the weld points on the first long side are adjacent to the corresponding weld points on the second long side to form a plurality of weld point pairs that are not all disposed on a single weld line having a longitudinal axis substantially parallel to the longitudinal axis of the mandrel. Each of the weld point pairs lies in a plane that is substantially parallel to the substantially flat surface of the mandrel. The weld point pairs may be connected by utilizing a laser beam directed substantially perpendicular to the plane containing the weld point pairs.

BRIEF DESCRIPTION OF THE DRAWINGS

The present invention will be understood and appreciated more fully from the following detailed description taken in conjunction with the drawings in which.

DETAILED DESCRIPTION OF THE INVENTION

Figure 1:
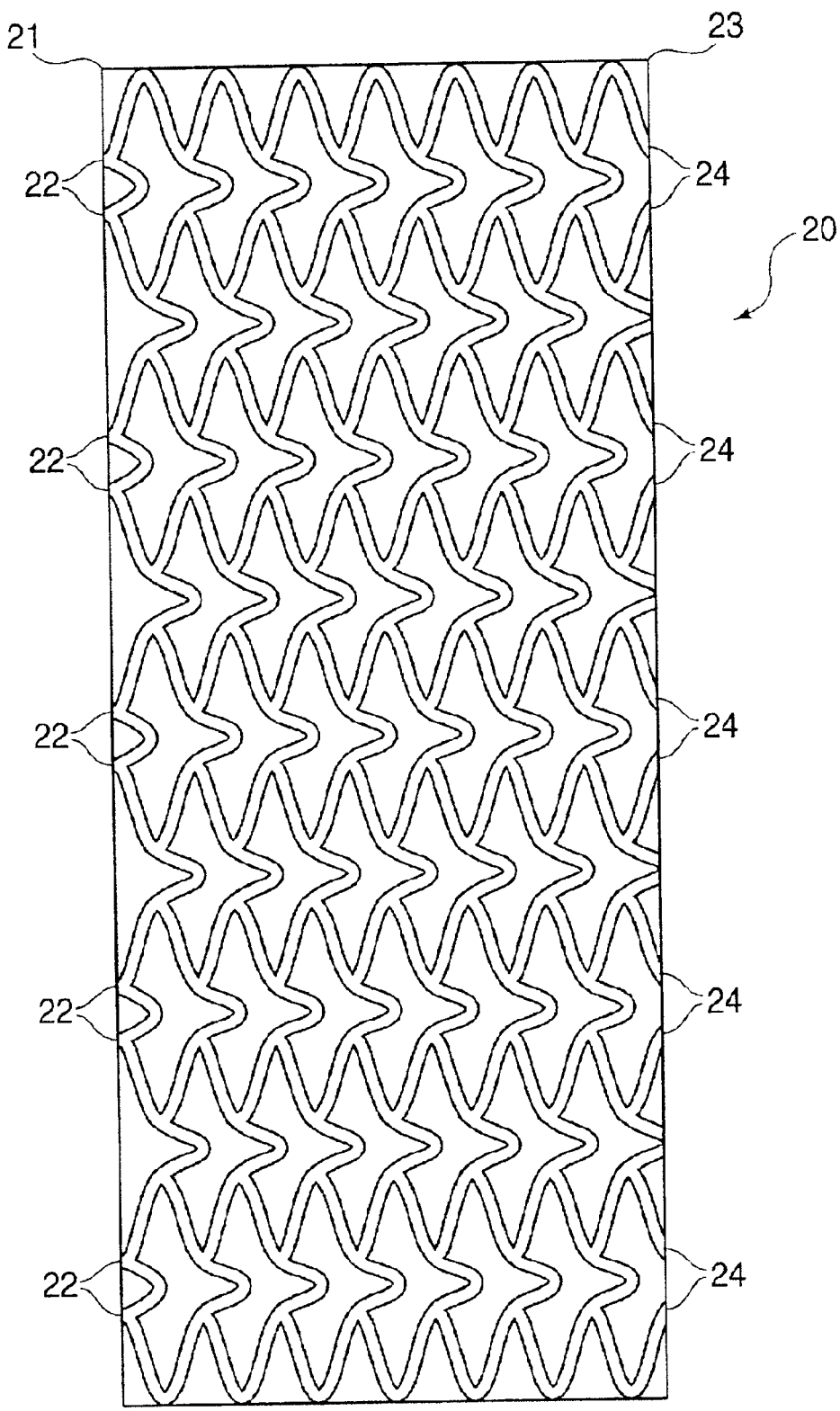
FIG. 1 shows a sheet utilized to make a stent.

FIG. 1 shows a sheet 20 used to fabricate a stent. The sheet 20 has a first long side 21 provided with a plurality of weld points 22 and a second long side 23 provided with a plurality of corresponding weld points 24. The sheet 20 may be provided with a variety of patterns as specific applications dictate. The sheet may be comprised of a variety of materials well known to those skilled in the art as suitable for this purpose, for example, metals or plastics. In one preferred embodiment, the sheet may be comprised of stainless steel. In another preferred embodiment, the sheet may be comprised of a super-elastic material such as nitinol which is an alloy of nickel and titanium.

Figure 2:
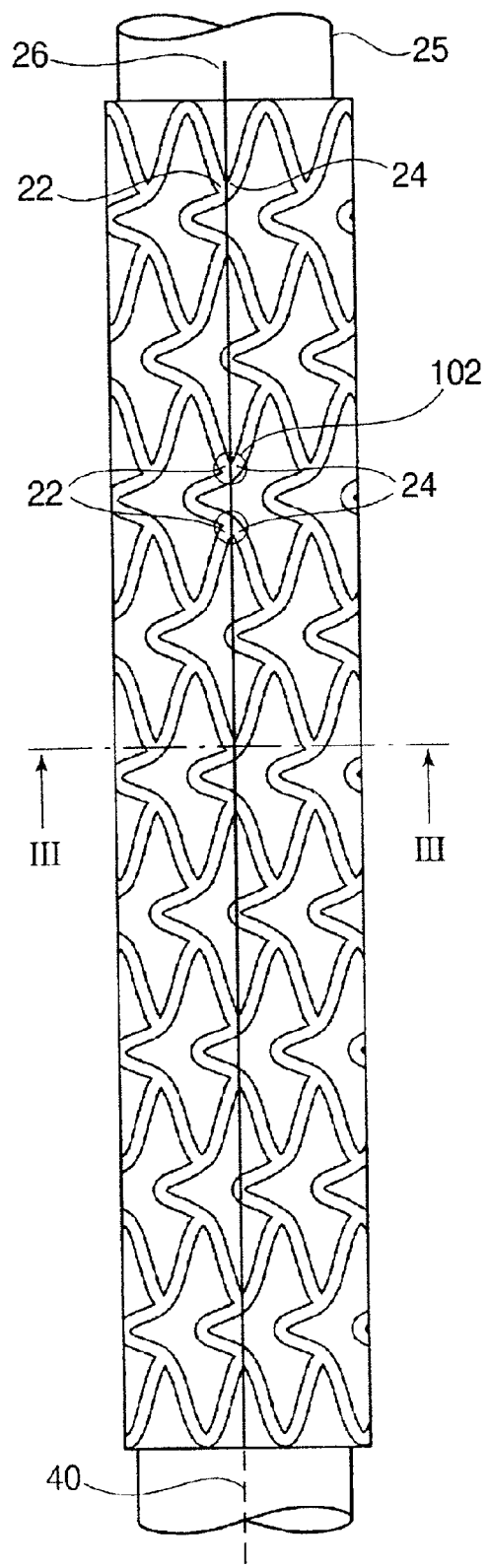
FIG. 2 shows the sheet of FIG. 1 after it has been wrapped around a conventional mandrel.

FIG. 2 is a top view of the sheet 20 of FIG. 1 and shows how the sheet 20 appears after it has been rolled into a substantially tubular shape and wrapped around a conventional mandrel 25 which has a longitudinal axis 40 and a substantially circular cross-sectional shape. FIG. 2 shows that the corresponding weld points 22 and 24 when adjacent to each other form a weld point pair 102. Each of the corresponding weld points 22 and 24 comprising a plurality of weld point pairs 102 is disposed along a single weld line 26 disposed along the longitudinal axis 40 of the mandrel 25.

Figure 3:
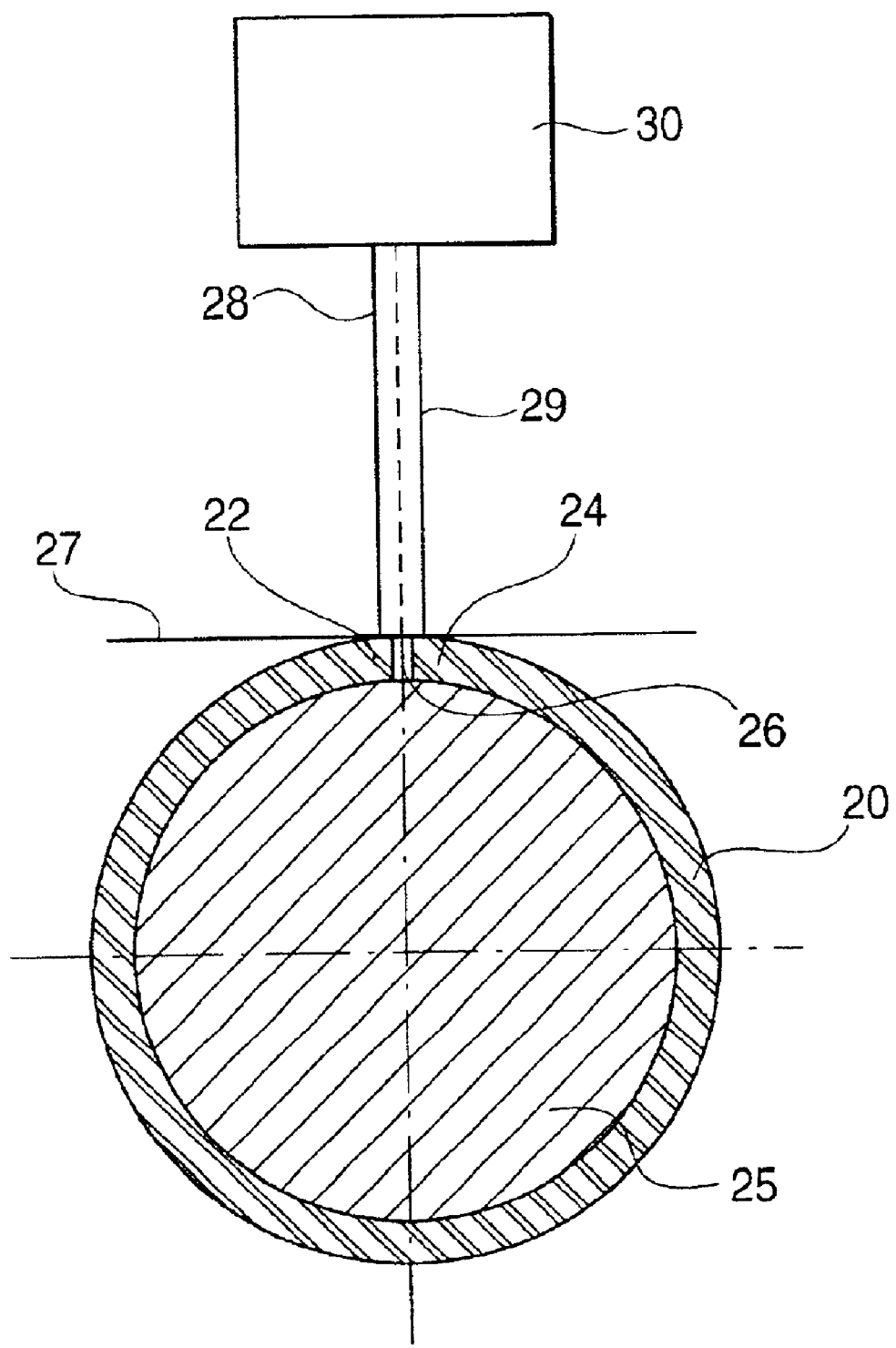
FIG. 3 is an enlarged cross-sectional view of FIG. 2 taken along line 3—3 of FIG. 2.

FIG. 3 is an enlarged cross-sectional view taken along line 3—3 of FIG. 3. The welding plane 27 is a plane that forms a tangent with the corresponding weld points 22 and 24 comprising weld point pairs 102. FIG. 3 shows that the weld points 22 and 24 lie in a welding plane 27 that intersects the means for joining that may be a laser beam 29. The welding plane 27 is disposed at an angle that is substantially perpendicular to the laser beam 29 used to join the corresponding weld points 22 and 24 comprising the weld point pairs 102. It is desirable that the laser beam 29 be directed at an angle that intersects the welding plane 27 at an angle that is substantially perpendicular to the welding plane 27 in order to optimize the efficiency, uniformity, and strength of the weld between the weld points 22 and 24.

Figure 4:
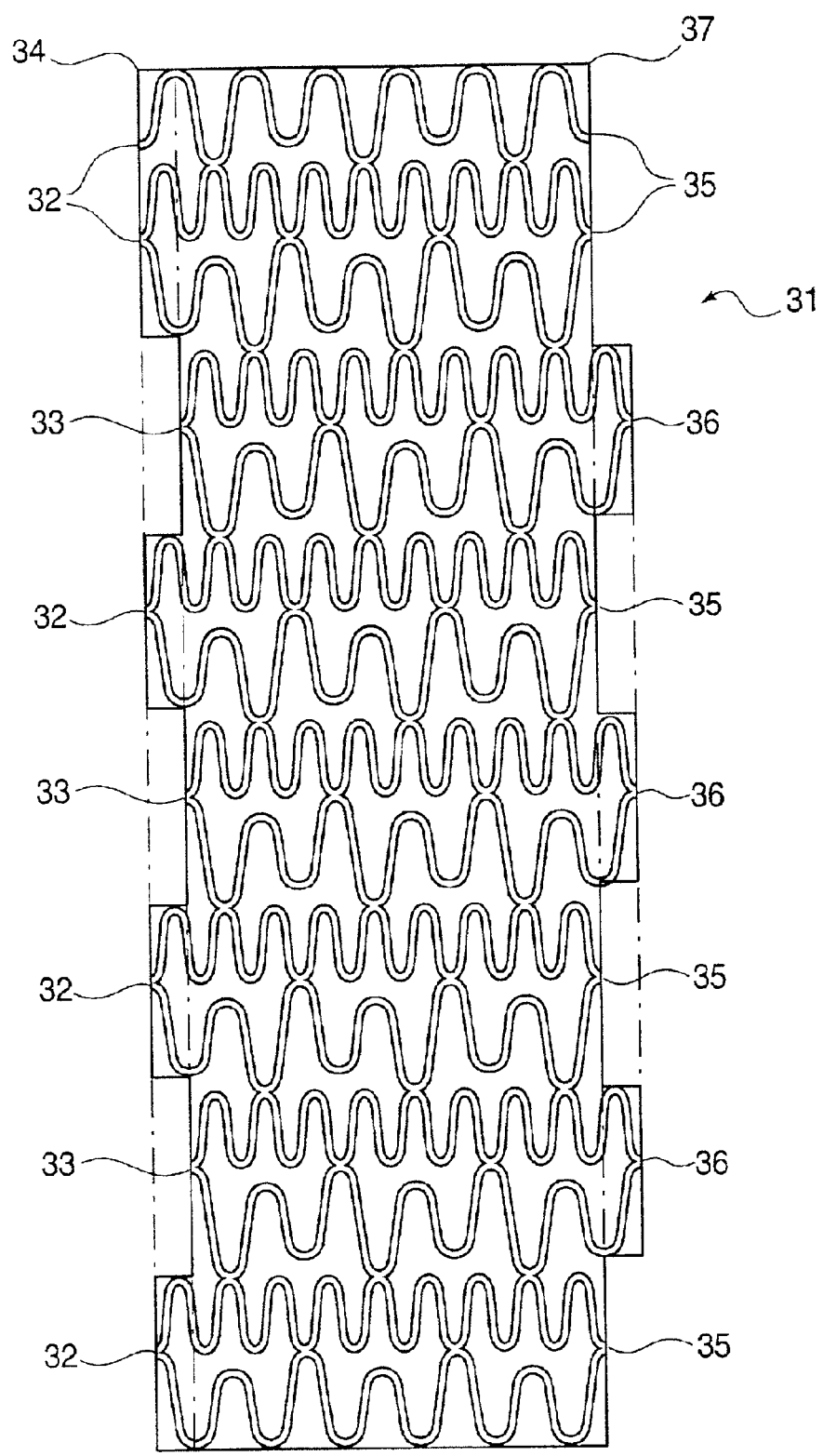
FIG. 4 shows one embodiment of a sheet that may be utilized to make a stent in accordance with the invention.

In some applications it may be desirable to manufacture stents whose weld point pairs do not all lie on a single line parallel to the longitudinal axis of the mandrel, or that are provided with more than one weld line. FIG. 4 shows one embodiment of a sheet that can be used to fabricate a stent in accordance with the invention. The sheet 31 has a plurality of first weld points 32 and second weld points 33 on the first long side 34 and a plurality of first weld points 35 and second weld points 36 on the second long side 37.

Figure 5:
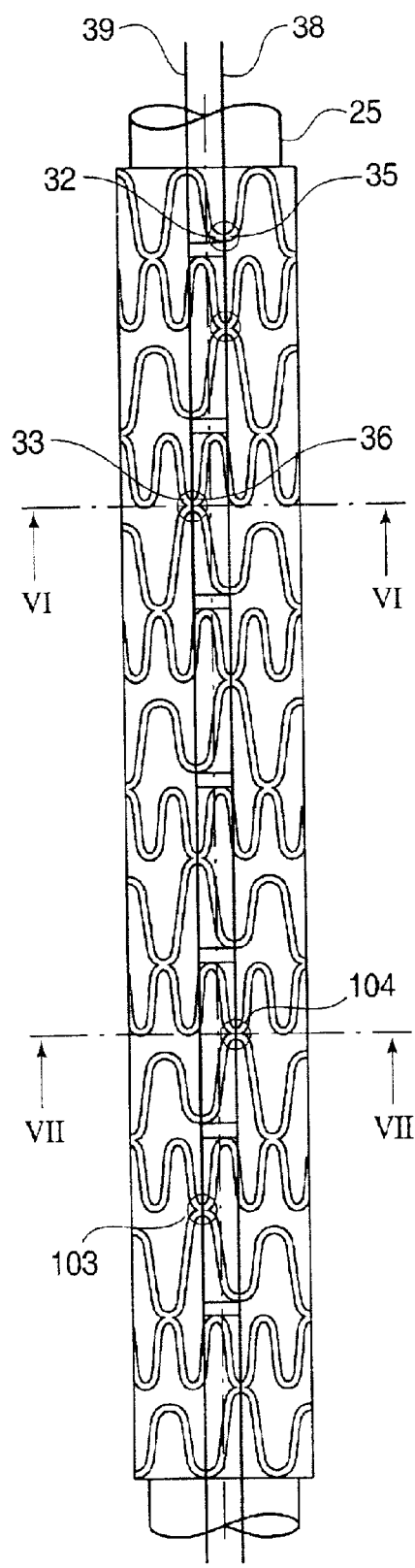
FIG. 5 shows the sheet of FIG. 4 after it has been wrapped around a conventional mandrel.

FIG. 5 is a top view of the sheet 31 of FIG. 4 after it has been rolled into a substantially tubular form and wrapped around a conventional mandrel 25 having a substantially circular cross sectional shape. The first weld line weld point 32 and its corresponding first weld line weld point 35 comprise weld point pair 104 and are disposed and aligned along a first weld line 38. The second weld line weld point 33 and its corresponding second weld line weld point 36 comprise weld point pair 103 and are disposed and aligned along a second weld line 39.

Figure 6:
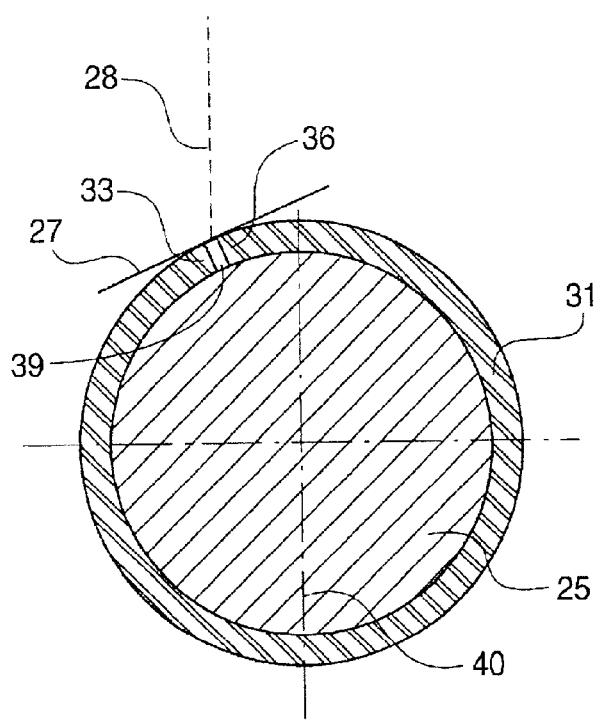
FIG. 6 is an enlarged cross-sectional view of FIG. 5 taken along line 6—6 of FIG. 5.

FIG. 6 is an enlarged cross-sectional view taken along line 6—6 of FIG. 5. As shown in FIG. 6, when the laser 30 has been moved laterally from the longitudinal axis 40 of the conventional mandrel 25 so as to weld the second weld line weld points 33 and 36 disposed on the second weld line 39, the angle made by the longitudinal axis 28 of the laser beam 29 is not substantially perpendicular to the welding plane 27 when it intersects the welding plane 27 of the second weld points 33 and 36 disposed on the second weld line 39.

Figure 7:
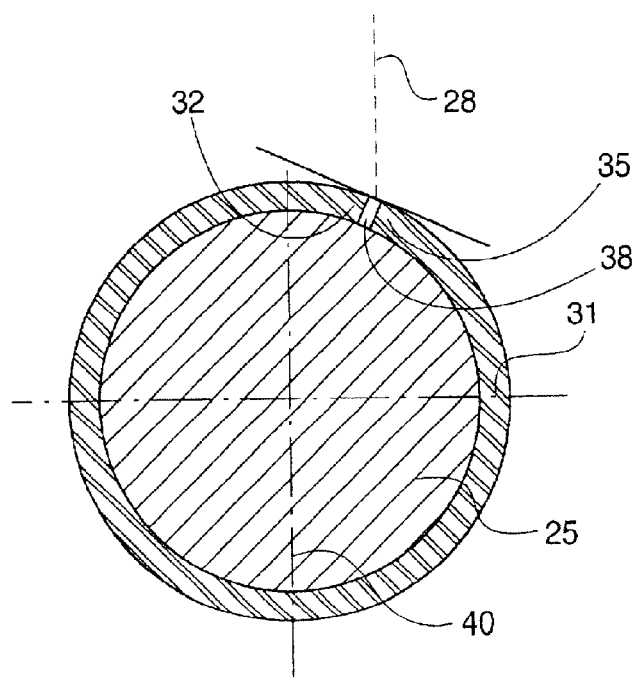
FIG. 7 is an enlarged cross-sectional view of FIG. 5 taken along lines 7—7 of FIG. 5.

FIG. 7 is an enlarged cross-sectional view taken along line 7—7 of FIG. 5. As shown in FIG. 7, when the laser has been moved laterally from the longitudinal axis 40 of the conventional mandrel 25 so as to weld the first weld line weld points 32 and 35 on the first weld line 38, the angle made by the longitudinal axis 28 of the laser beam 29 when it intersects the welding plane of the first weld points 32 and disposed on the first weld line 38 is not substantially perpendicular to the weld plane 27. A laser beam is directed at the weld planes 27 of the weld point pairs 103, 104 disposed along the weld lines 38, 39 so that the laser beam is at an angle that is not substantially perpendicular to the welding planes 27. This could result in less efficient, irregular welds having less than optimal strength. Thus, using conventional methods and conventional devices for manufacturing stents made from sheets having weld point pairs disposed on more than one weld line, or having weld point pairs that are not disposed along a single weld line, may produce stents that are less uniform and have inferior welds.

Figure 8:
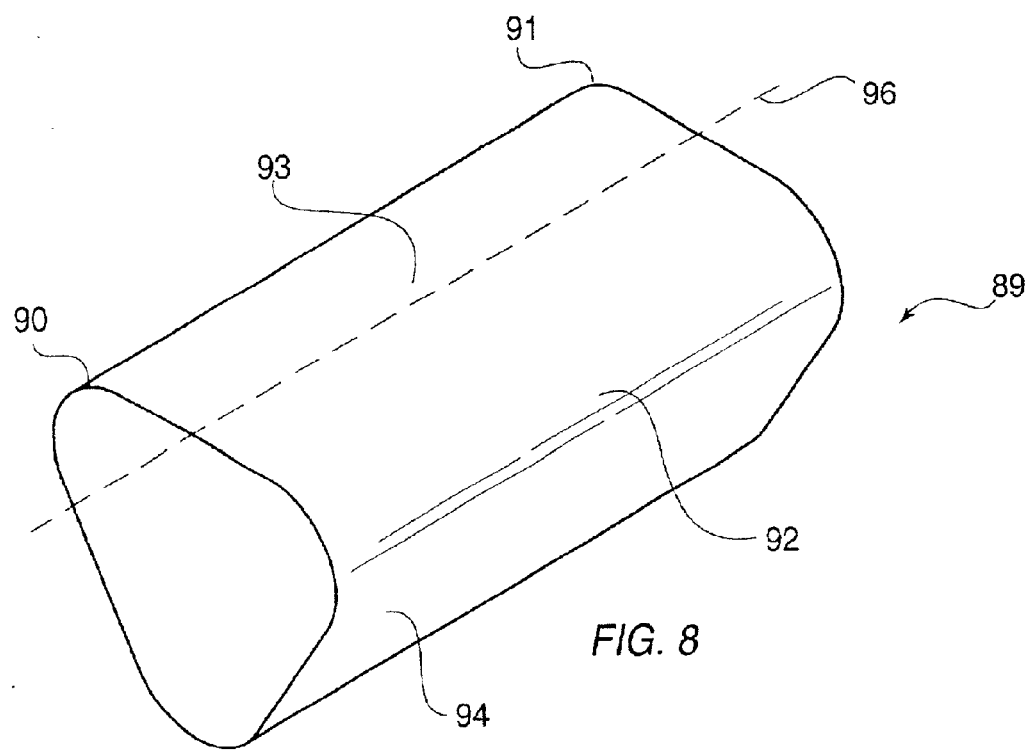
FIG. 8 is a perspective view of a preferred embodiment of a mandrel constructed in accordance with the invention.
Figure 9:
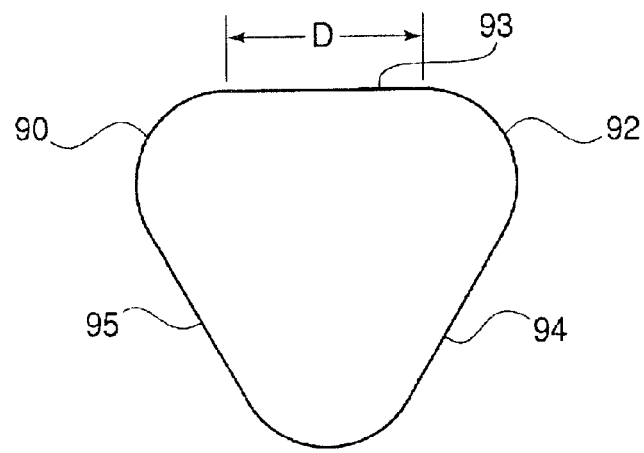
FIG. 9 is a cross-sectional view of the mandrel of FIG. 8.

FIGS. 8 and 9 show a preferred embodiment of a mandrel 89 constructed in accordance with the invention. FIG. 8 is a perspective side view and shows a first end 90, a second end 91, an external surface 92, a longitudinal axis 96, a first substantially flat major surface 93 disposed between the first end 90 and the second end 91, and a second substantially flat major surface 94 disposed between the first end 90 and the second end 91. FIG. 9 is an end view of FIG. 8 and shows a first end 90, an external surface 92, a first substantially flat major surface 93, a second substantially flat major surface 94, and a third substantially flat major surface 95. In a preferred embodiment, the substantially flat major surface 101 has a width W that is wide enough to accommodate the weld point pairs. Although the preferred embodiment of a mandrel shown in FIGS. 8 and 9 shows three substantially flat major surfaces, the invention may be practiced with a mandrel provided with more than three, or less than three, substantially flat major surfaces depending upon the requirements of specific applications.

Figure 8A:
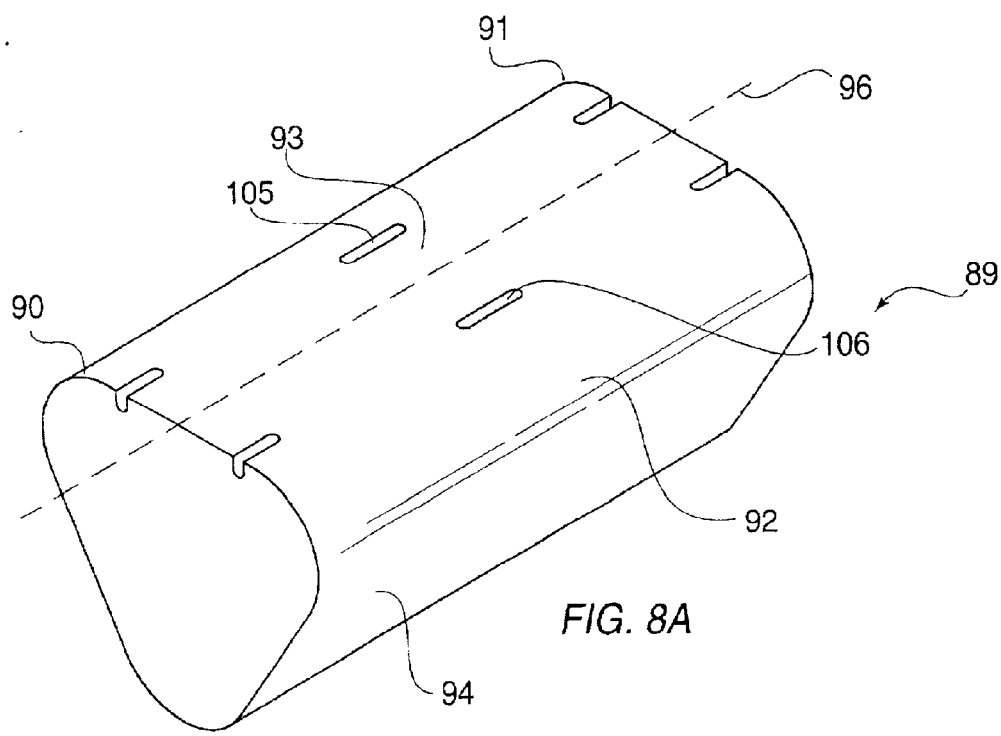
FIG. 8A shows an alternative embodiment of the mandrel shown in FIG. 8.
Figure 9A:
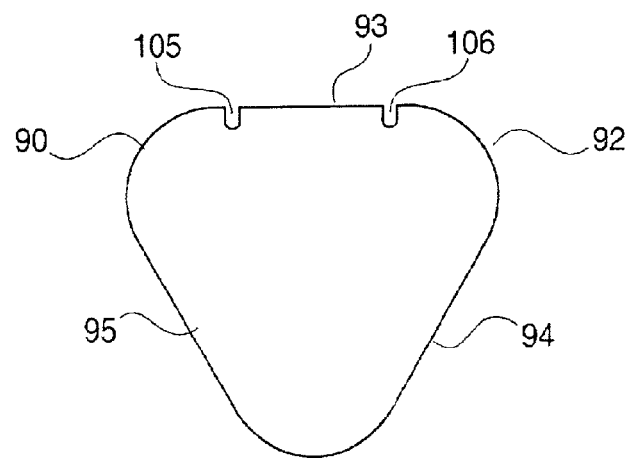
FIG. 9A is an end view of the alternative embodiment shown in FIG. 8A.

FIGS. 8A and 9A show an alternative embodiment of the invention in which the substantially flat major surface 93 of the mandrel 89 is provided with a plurality of voids or recesses 105, 106. The voids 105 and 106 are sized and disposed on the substantially flat major surface 93 so that they will be substantially in registry with, and be disposed substantially beneath, the weld point pairs when a sheet is wrapped around the mandrel 89. The voids 105, 106 may allow for additional weld material to form against the major surface of the sheet that faces the substantially flat surface 93 of the mandrel 89 which produces a stronger weld. The voids 105, 106 may also minimize the heat transfer from the weld to the mandrel and, thus, may reduce the amount of energy that must be put into the weld. The number of voids can be varied as specific applications dictate, however, in a preferred embodiment one void is provided for each weld point pair. The voids 105, 106 may be provided in one or more of the substantially flat major surfaces 91, 94, 95.

Figure 8B:
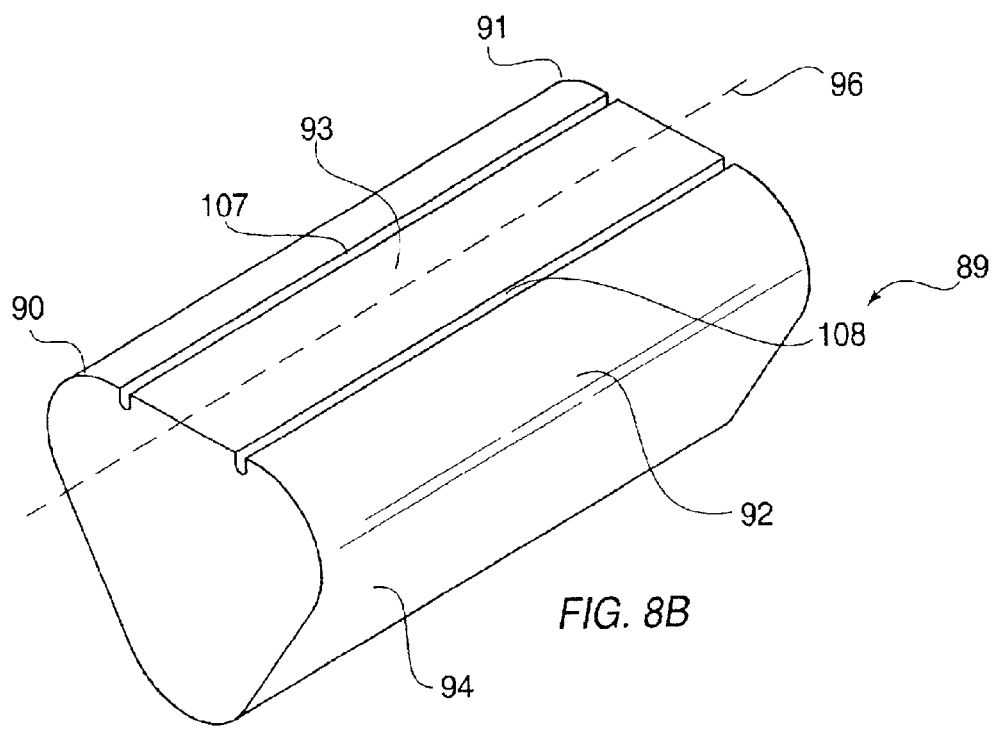
FIG. 8B shows an alternative embodiment of the mandrel shown in FIG. 8.
Figure 9B:
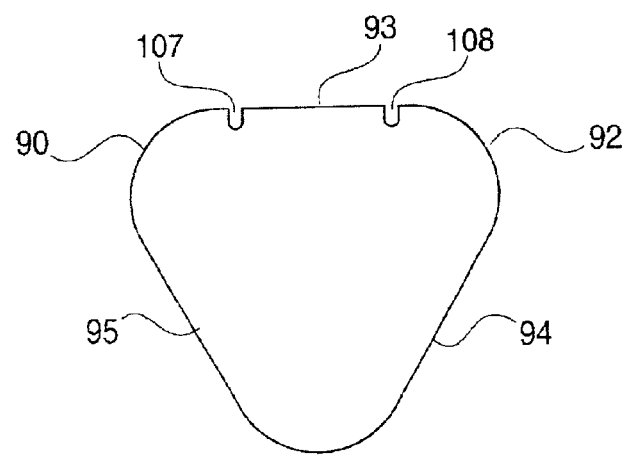
FIG. 9B is an end view of the alternative embodiment shown in FIG. 8B.

FIGS. 8B and 9B show another alternative embodiment of the invention in which the substantially flat major surface 93 of the mandrel 89 is provided with a plurality of grooves 107, 108. This embodiment may be especially useful when the weld point pairs are disposed along one or more weld lines. The grooves 107, 108 are sized and disposed on the substantially flat major surface 93 so that they will be substantially in registry with, and be disposed substantially beneath, the weld point pairs when a sheet is wrapped around the mandrel 89. The grooves 107, 108 may allow for additional weld material to form against the major surface of the sheet that faces the substantially flat surface 93 of the mandrel 89 which may produce a stronger weld. The grooves 107, 108 may also minimize the heat transfer from the weld to the mandrel and, thus, may reduce the amount of energy that must be put into the weld. The number of grooves can be varied as specific applications dictate, however, in a preferred embodiment a groove is provided for each weld line. The grooves 107, 108 may be provided in one or more of the substantially flat major surfaces 91, 94, 95.

Figure 10:
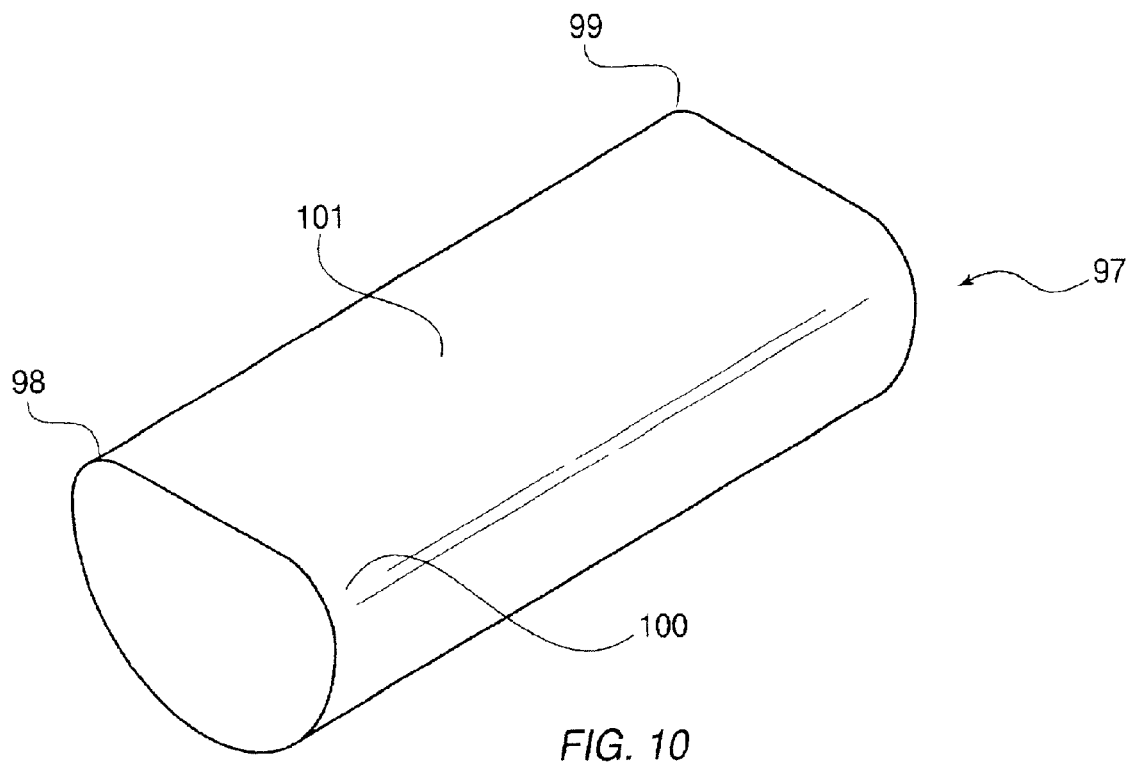
FIG. 10 is a perspective view of an alternative embodiment of a mandrel constructed in accordance with the invention.
Figure 11:
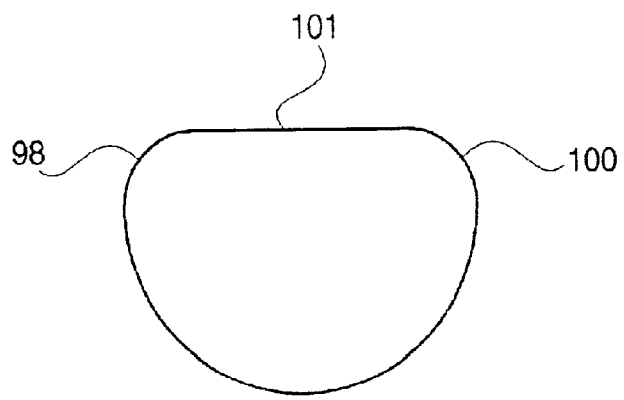
FIG. 11 is a cross-sectional view of the mandrel of FIG. 10.

FIGS. 10 and 11 show an alternative embodiment of a mandrel 97 constructed in accordance with the invention wherein the mandrel 97 is provided with a single, substantially flat major surface 101. FIG. 10 is a perspective side view and shows a first end 98, a second end 99, an external surface 100, and a substantially flat major surface 101. FIG. 11 is an end view of FIG. 10 and shows a first end 98, an external surface 88, and a substantially flat major surface 101. The embodiment of FIGS. 10 and 11 may be provided with one or more voids or grooves as previously discussed.

Figure 12:
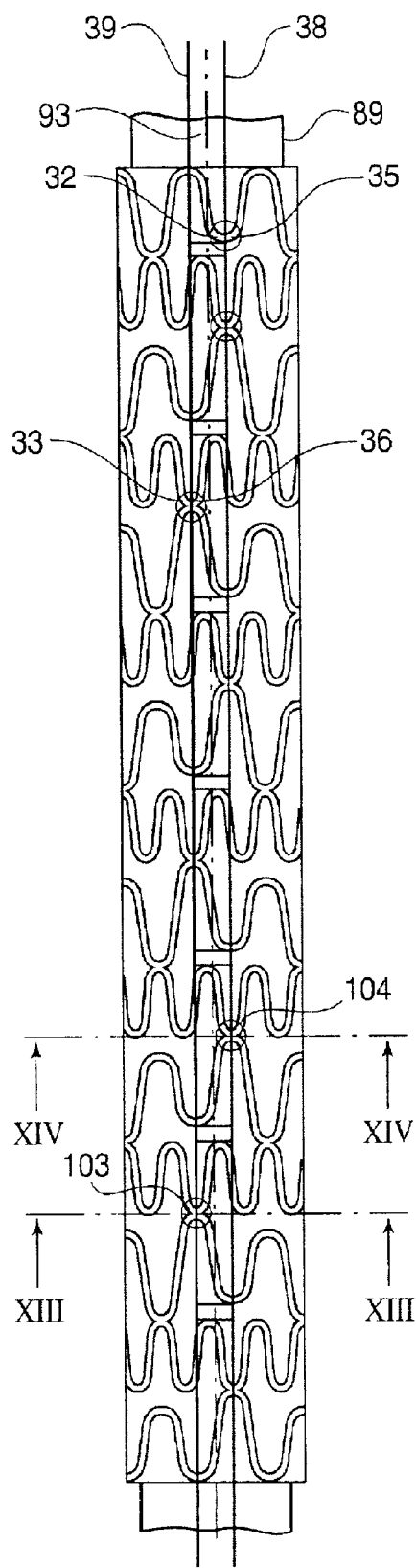
FIG. 12 is a top view of the sheet of FIG. 4 after it has been wrapped around the mandrel of FIG. 8.

FIG. 12 is a top view of the sheet 31 of FIG. 4 after it has been rolled into a substantially tubular shape and wrapped around or applied to the mandrel 89 of FIG. 8. FIG. 12 shows that the first weld point 32 and its corresponding weld point 35 comprising weld point pair 104 are disposed on the first weld line 38. FIG. 12 also shows that the second weld points 33 and 36 comprising weld point pair 103 are disposed on the second weld line 39. As shown, both the first weld line 38 and the second weld line 39 lie within the borders of the substantially flat major surface 93.

Figure 12A:
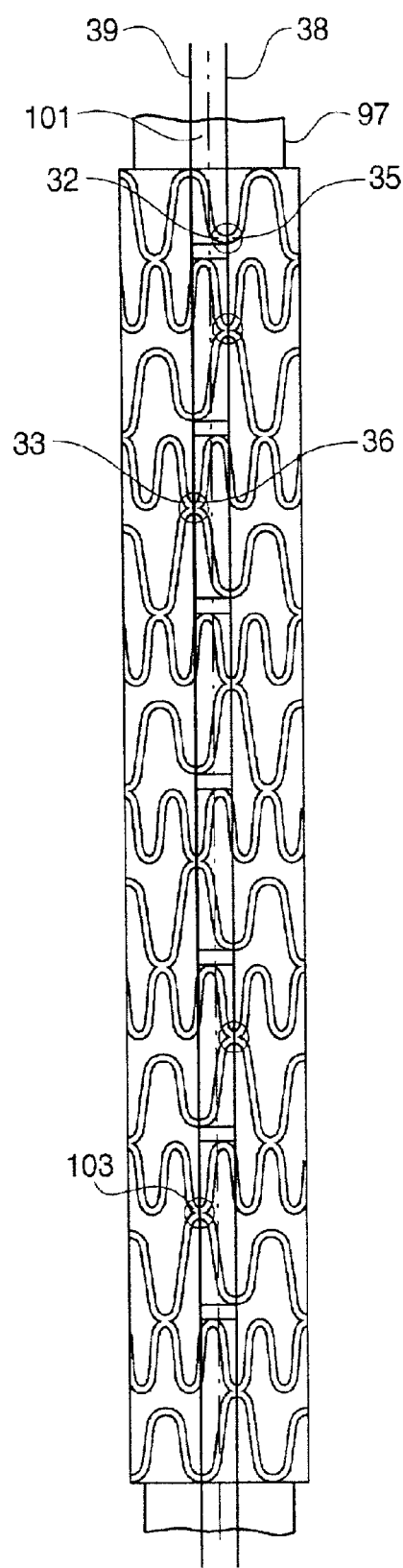
FIG. 12A is a top view of the sheet of FIG. 4 after it has been wrapped around the mandrel of FIG. 10.

FIG. 12A is a top view of the sheet 31 of FIG. 4 after it has been rolled into a substantially tubular shape and wrapped around or applied to the mandrel 97 of FIG. 10. FIG. 12A shows that the first weld point 32 and its corresponding weld point 35 comprising weld point pair 104 are disposed on the first weld line 38. FIG. 12 also shows that the second weld points 33 and 36 comprising weld point pair 103 are disposed on the second weld line 39. As shown, both the first weld line 38 and the second weld line 39 lie within the borders of the substantially flat major surface 101.

Figure 13:
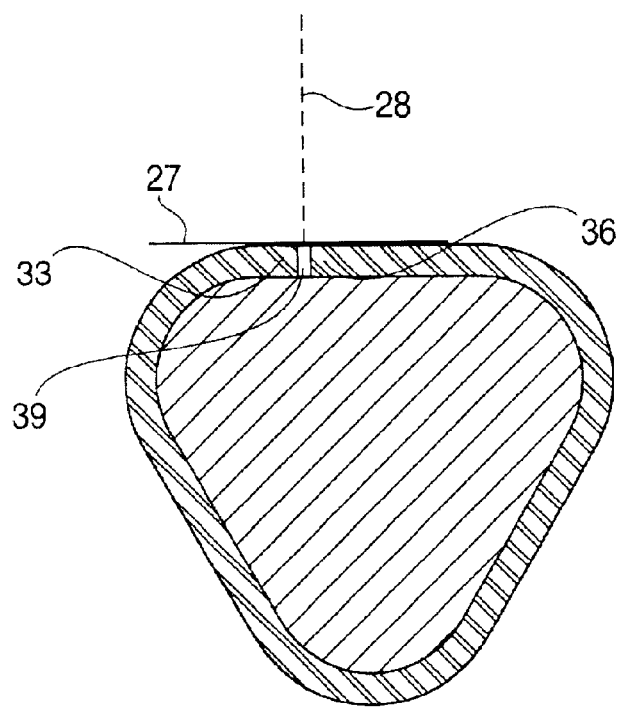
FIG. 13 is an enlarged cross-sectional view of FIG. 12 taken along line 13—13 of FIG. 12.

FIG. 13 is a cross-sectional view taken along line 13—13 of FIG. 12. FIG. 13 shows that when the laser 30 is moved laterally from the longitudinal axis 96 of the mandrel 89 to weld the corresponding weld points 33 and 36 disposed on the second weld line 39 of the sheet 31, the laser beam 29 is substantially perpendicular to the welding plane 27 of the weld points 33 and 36 comprising weld point pairs 103 disposed along the second weld line 39.

Figure 14:
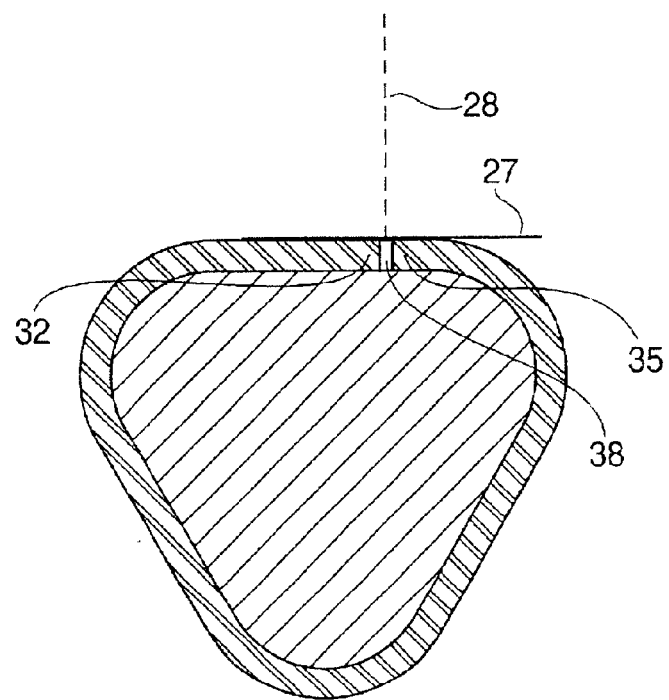
FIG. 14 is an enlarged cross-sectional view of FIG. 12 taken along line 14—14 of FIG. 12.

FIG. 14 is a cross-sectional view taken along line 14—14 of FIG. 12. FIG. 14 shows that when the laser 30 has moved laterally from the longitudinal axis 96 of the mandrel 89 to weld the corresponding weld points 32 and 35 comprising weld point pair 104 disposed on the first weld line 38 of the sheet 31, the laser beam 29 is substantially perpendicular to the welding plane 27 of the weld points 32 and 35 disposed along the first weld line 38.

Although the preferred embodiment of the invention discussed above utilizes laser welding to join the weld points, the weld points may also be joined by other means that are well known to those skilled in the art as suitable for this purpose, for example, spot-welders, arc-welders, and gluing devices.

Because the laser beam 29 intersects the welding planes 27 at an angle that is substantially perpendicular to the welding planes 27 of the weld points 32 and 35 on the first weld line 38 and weld points 33 and 36 on the second weld line 39, more uniform and stronger welds result and, thus, more uniform and stronger stents are produced.

It will be appreciated by those skilled in the art that sheets having a variety of arrangements and patterns of weld points and weld lines may be utilized to manufacture stents in accordance with this invention. Of course, the weld points on the first long side and the second long side need not actually be disposed on lines at all; they need only meet in weld point pairs when the sheet is rolled into a tubular shape and the first and second long sides meet each other. In some applications it may be desirable to manufacture stents in which no two weld point pairs are disposed along an axis that is substantially parallel to the longitudinal axis of the mandrel. In other applications it may be desirable to manufacture stents in which the weld points are disposed along a plurality of weld lines substantially parallel to the longitudinal axis of the mandrel.

Figure 15:
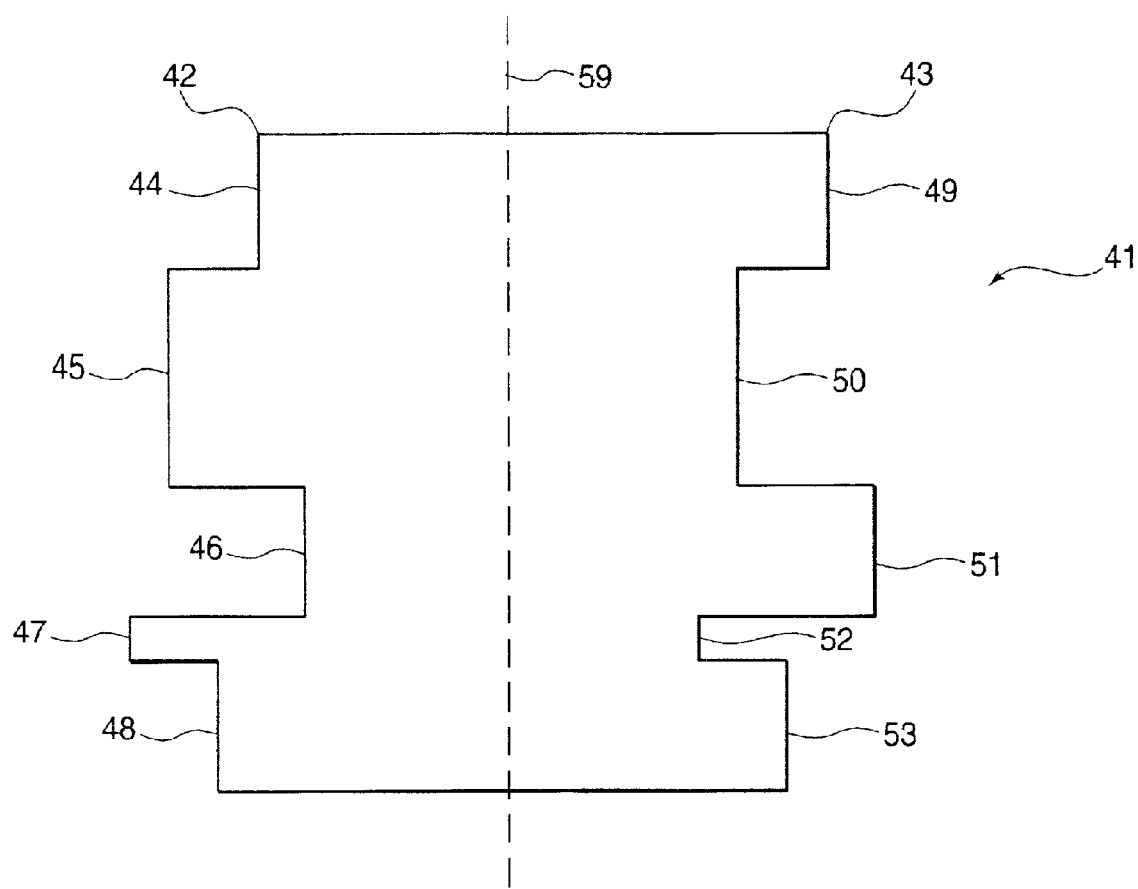
FIG. 15 shows an illustrative pattern of a sheet that might be accommodated in accordance with the invention.
Figure 16:
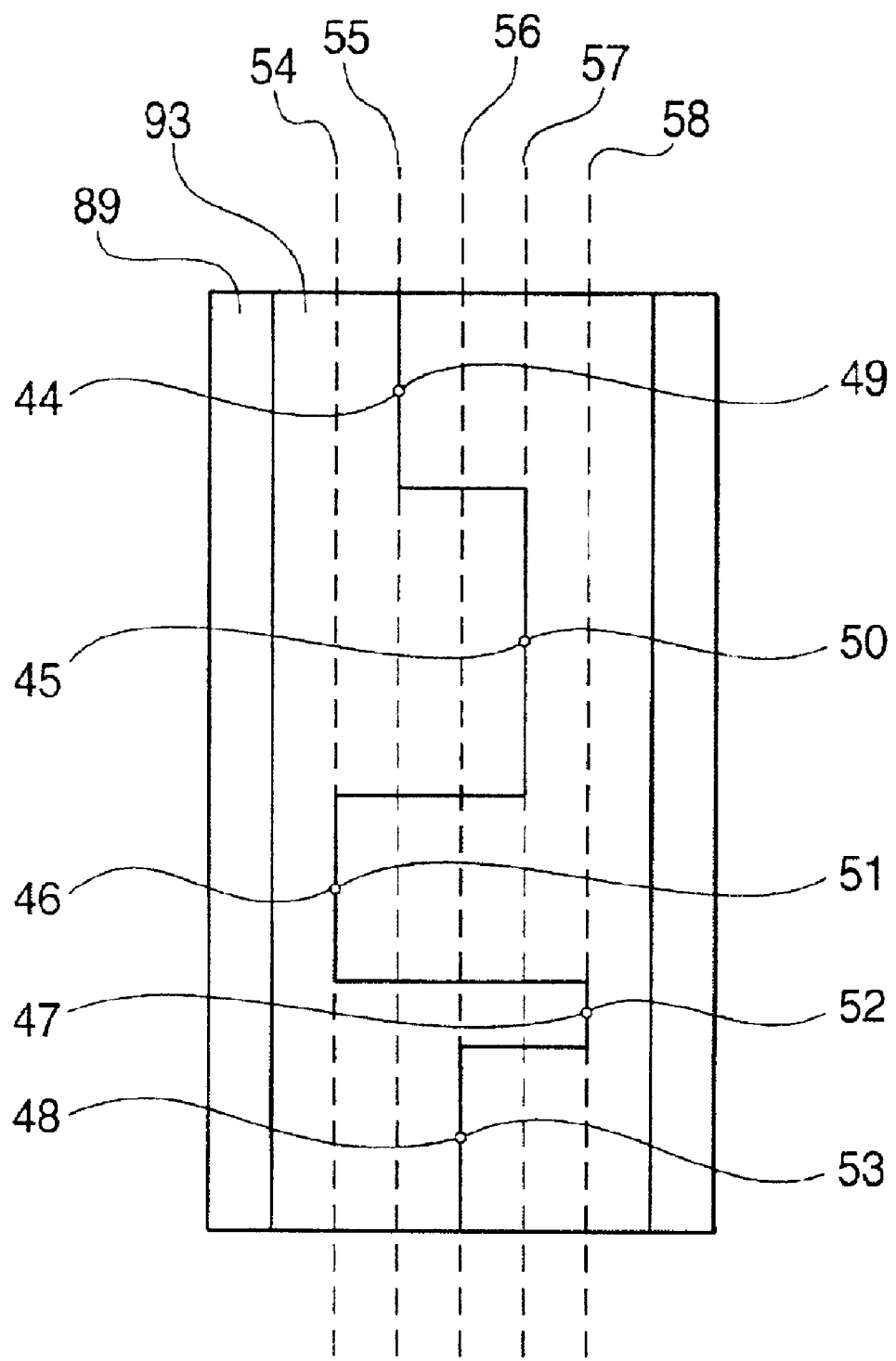
FIG. 16 shows the sheet of FIG. 15 after it has been rolled into a tubular shape.

FIG. 15 shows a simplified representation of one such embodiment of a sheet 41 having an arrangement of weld points comprising a plurality of weld point pairs that are not disposed on a single weld line having a longitudinal axis parallel to the longitudinal axis of the sheet 41. The sheet 41 has a first long side 42 and a second long side 43 and a longitudinal axis 59 and is provided with weld points 44, 45, 46, 47, and 48 disposed along the first long side 42. Corresponding weld points 49, 50, 51, 52, and 53 disposed along the second long side 43. FIG. 16 is a top view of the sheet of FIG. 8 after it has been rolled into a substantially tubular shape and wrapped around a mandrel 89 constructed in accordance with the invention. FIG. 16 shows that the corresponding-weld points 44 and 49, 45 and 50, 46 and 51, 47 and 52, and 48 and 53 have been aligned and form weld point pairs. As shown in FIG. 16, when the sheet 41 is rolled into a substantially tubular shape no two weld point pairs are aligned along a single weld line parallel to the longitudinal axis 59 of the sheet 41. Instead, the weld point pairs are independently arranged along five different weld lines 54, 55, 56, 57, and 58. Nonetheless, the weld lines 54, 55, 56, 57, and 58 lie within the substantially flat major surface 93 of the mandrel, and therefore the laser beam 29 will be substantially perpendicular to the weld planes of the weld point pairs that are disposed on weld lines 54, 55, 56, 57, and 58.

Figure 17:
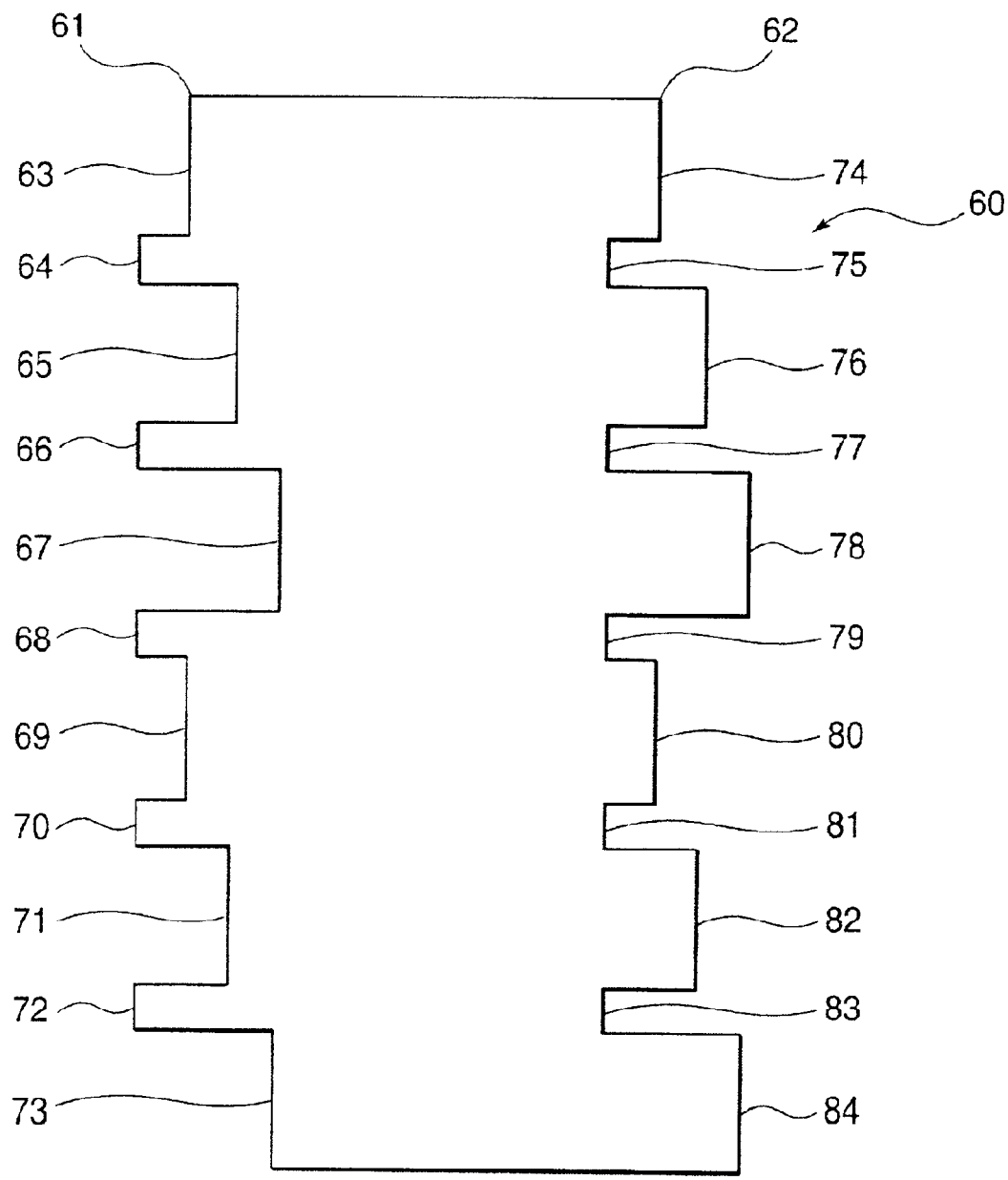
FIG. 17 shows a pattern for an alternative embodiment of a sheet utilized to make a stent in accordance with the invention.
Figure 18:
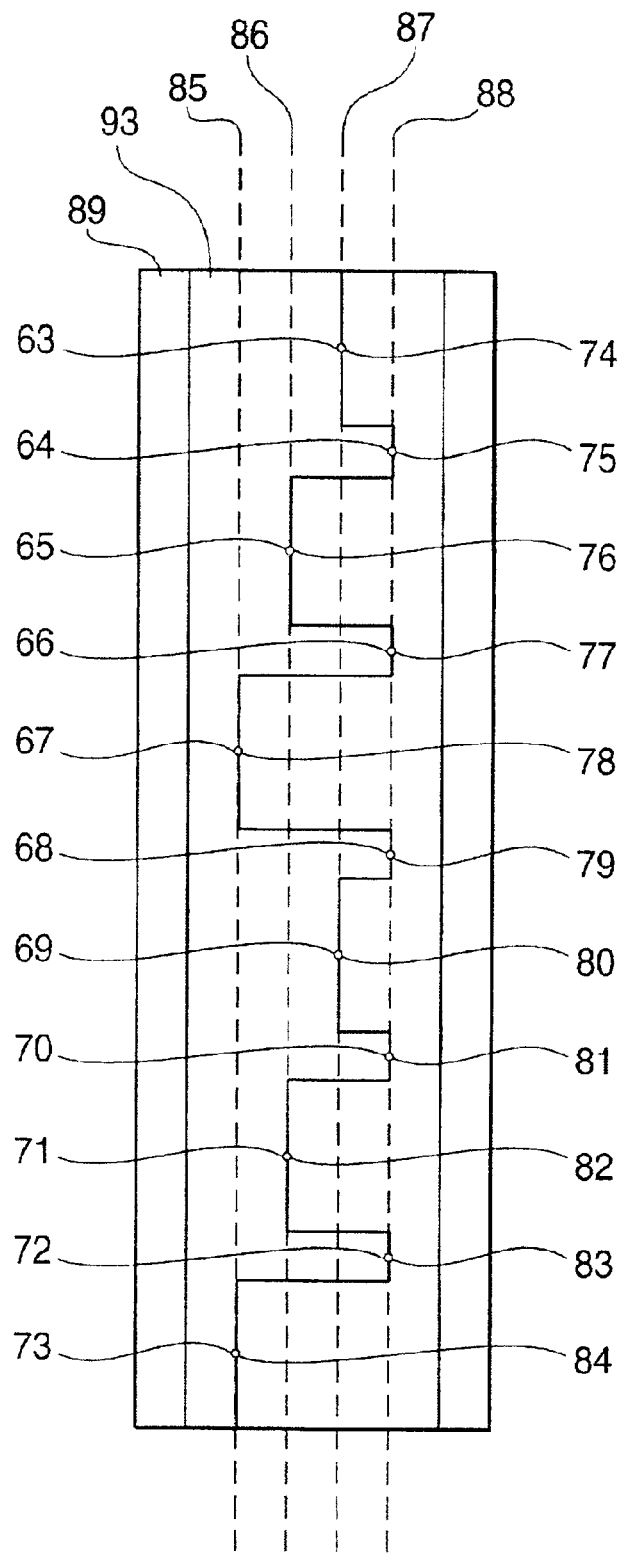
FIG. 18 shows the sheet of FIG. 17 after it has been rolled into a tubular shape.

FIG. 17 shows a simplified representation of one embodiment of a sheet 60 having weld points arranged along four weld lines. The sheet 60 has a first long side 61 and a second long side 62. A plurality of weld points 63, 64, 65, 66, 67, 68, 69, 70, 71, 72, and 73 are disposed along the first long side 61 and a plurality of weld points 74, 75, 76, 77, 78, 79, 80, 81, 82, 83, are 84 disposed along the second long side. FIG. 18 shows the sheet 60 of FIG. 17 after it has been rolled into a substantially tubular shape and wrapped around the mandrel 89 of FIG. 8 constructed in accordance with the invention. As shown in FIG. 18, in this embodiment when the sheet 60 has been rolled into a substantially tubular shape the weld point pairs are disposed along four weld lines 85, 86, 87, and 88. Again, because the weld lines 85, 86, 87, and 88 are disposed within the substantially flat surface 93 of the mandrel 89, the laser beam 29 is substantially perpendicular to the weld point pairs disposed along the welding lines 85, 86, 87, and 88.

If, instead, the sheets 41 and 60 of FIGS. 15 and 17 were to be wrapped around a conventional mandrel having a substantially circular cross-section, the same problem would occur with respect to the angle that the laser beam makes when it intersects the welding plane of the weld points as discussed above with respect to FIG. 4. Thus, as shown in FIGS. 12, 16, and 18, no matter how many weld lines are utilized for a specific application, the present invention may optimize the uniformity and strength of all of the welds on all of the weld lines.

In an especially preferred embodiment of the invention, the weld points comprising the weld point pairs are disposed to form a v-shaped notch prior to joining. This results in a stronger joint.

A detailed discussion of methods of making stents and approaches for making stents is found in U.S. Pat. No. 5,906,759 the specification of which has been incorporated herein by reference.

To practice a preferred embodiment of the invention a patterned sheet having a first long side and a second long side is utilized. The first long side is provided with a plurality of weld points that correspond to a plurality of weld points disposed on the second long side. When the sheet is rolled into a substantially tubular shape the corresponding weld points are aligned and form a plurality of weld point pairs. The weld points comprising the weld point pairs are arranged so that when the sheet is rolled into a tubular configuration, the weld point pairs are not all located on a single weld line. A means for wrapping is used to wrap the sheet around the mandrel. The means for wrapping may be selected from a wide variety of means for wrapping well known to those skilled in the art, however, in a preferred embodiment one or more deforming blades is utilized. The mandrel has a first end, a second end, and is provided with at least one substantially flat major surface disposed between the first end and the second end. The sheet is wrapped around the mandrel so that all of the weld lines are disposed adjacent to the substantially flat surface. An aligning and securing means, preferably a selectively actuated blade, is utilized to align and secure the weld points on the first long side of the sheet with the corresponding weld points on the second long side of the sheet. The aligned and secured weld points form a plurality of weld point pairs so that all of the weld planes of all of the weld points comprising the weld point pairs disposed on all of the weld lines are substantially parallel to the plane of the substantially flat major surface of the mandrel. A means for joining, preferably one or more lasers, may be disposed adjacent the mandrel and is supported for movement in directions parallel to and orthogonal to the longitudinal axis of the mandrel and the substantially flat major surface of the mandrel to permit the laser to migrate to a position above each weld point pair disposed on all of the weld lines. Alternatively, a plurality of fixed or movable lasers may be utilized. In yet another embodiment, the mandrel may be selectively moved to align the weld points with the laser beam generated by the laser or lasers. The laser beam is aligned over each weld point pair and is aimed at a target weld spot disposed about equidistant from the weld points comprising each weld point pair. The laser is energized and generates a laser beam that intersects the weld planes of each of the weld point pairs at an angle that is substantially perpendicular to the welding planes of each of the weld point pairs. The laser is energized in an amount and for a period of time sufficient to connect the weld points comprising each weld point pair.

After welding is complete, the welded stent is then removed from the mandrel. If the stent is made from a sheet comprising a shape-memory or super elastic material such as nitinol, the stent will preferably assume a substantially tubular shape having a substantially circular cross-section after it has been removed from the mandrel. If the stent is made from a sheet comprised of a material such as plastic or stainless steel, it may be necessary to reshape the stent after it has been removed from the mandrel so that the stent has a substantially circular cross-section. This may be accomplished in a variety of ways well known to those skilled in the art. In a preferred embodiment, a shaping mandrel having a substantially circular cross-section is introduced into the longitudinal bore of the stent. Preferably, the shaping mandrel is provided with a cross-sectional diameter that is substantially equal to the desired internal cross-sectional diameter of the stent. Pressure is applied to the external surface of the stent so that the stent subtantially conforms to the external surface of the mandrel. This provides the stent with a cross-section that is substantially circular and also provides the stent with the desired internal cross-sectional diameter.

Figure 19:
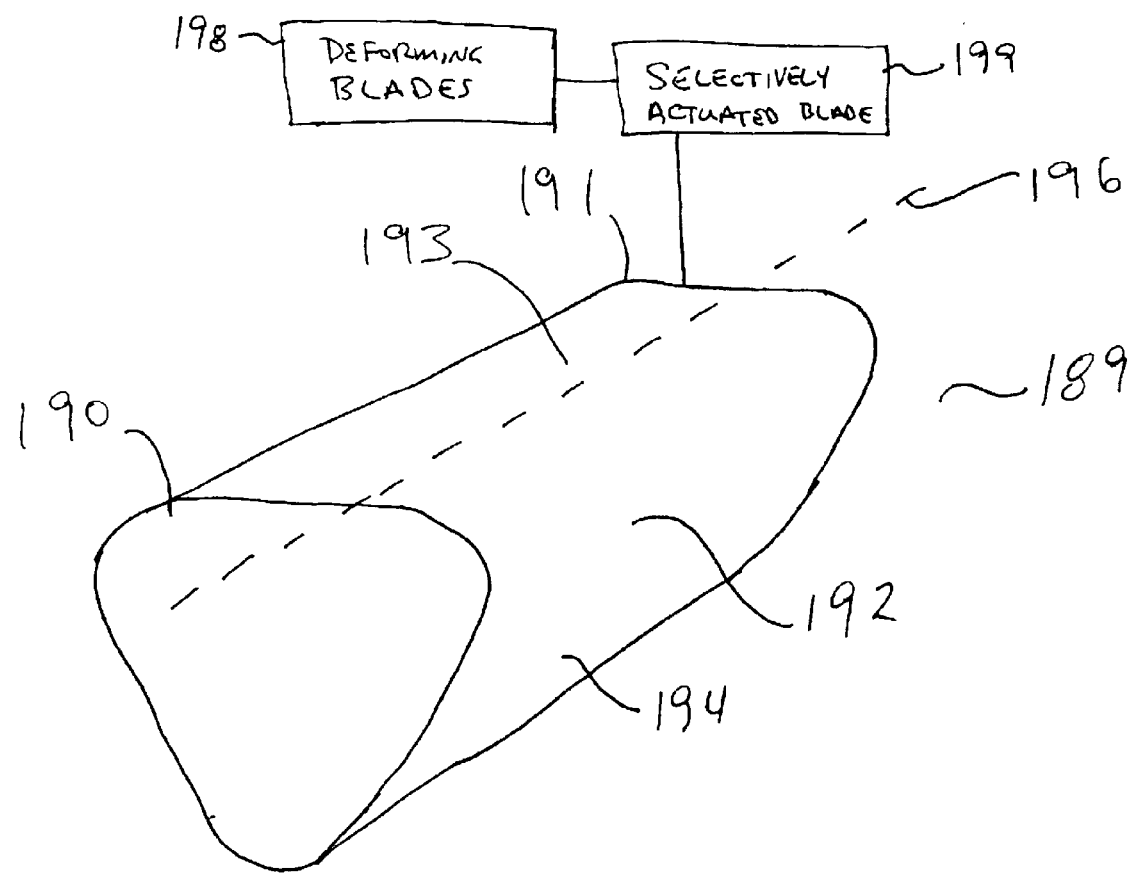
FIG. 19 is a perspective view of a preferred embodiment of a mandrel constructed in accordance with the invention.

FIG. 19 shows a preferred embodiment of a mandrel 189 constructed in accordance with the invention. FIG. 19 is a perspective side view and shows a first end 190, a second end 191, an external surface 192, a longitudinal axis 196, a first substantially flat major surface 193 disposed between the first end 190 and the second end 191, and a second substantially flat major surface 194 disposed between the first end 190 and the second end 191. FIG. 19 also shows, schematically, deforming blades 198 and selectively actuated blade 199.

Although certain preferred embodiments of the present invention have been described, the spirit and scope of the invention is by no means restricted to the preferred embodiments and examples disclosed above.

What is claimed is:

1. A mandrel for forming a stent, comprising:
a member having a first end, a second end and an external surface, the external surface provided with at least one substantially flat surface extending between the first end and the second end, the external surface configured to receive a sheet of material to be formed into the stent.

2. A mandrel for forming a stent, comprising:
a member having a first end and a second end and an external surface, the external surface provided with a plurality of substantially flat surfaces, each of the flat surfaces extending between the first end and the second end, the external surface configured to receive a sheet of material to be formed into the stent.

3. The mandrel of claim 1 or 2, wherein the mandrel is provided with three substantially flat surfaces.

4. The apparatus of claim 3, wherein the substantially flat surface of the mandrel is provided with one of: (a) at least one void; and (b) at least one groove having a longitudinal axis.

5. The apparatus of claim 4, wherein the longitudinal axis of the groove is substantially parallel to the longitudinal axis of the mandrel.

6. A mandrel for forming a stent comprising:
a longitudinal member having a first end and second end, the longitudinal member having a substantially triangular cross-sectional shape, wherein each of the three sides defining the substantially triangular shape is a substantially flat surface that extends between the first end and the second end of the mandrel;
wherein the sides are configured to receive a sheet of material to be formed into the stent.

7. The mandrel of claim 6, wherein a transition between adjacent flat surfaces is curved.

8. Apparatus comprising:
a) a mandrel having an axis, and having a substantially flat surface;
b) means to wrap a flat sheet provided with a stent pattern and having two opposed sides around the mandrel with the two opposed sides disposed on the flat surface; and
c) means for joining directed substantially perpendicular to the substantially flat surface.

9. The apparatus of claim 8, wherein the means for joining is a welding apparatus.

10. The apparatus of claim 9, wherein the welding apparatus is a laser-welding apparatus.

11. The apparatus of claim 8, wherein the means for joining is a gluing apparatus.

12. The apparatus of claim 8, wherein the means for joining is supported for movements in directions parallel to and orthogonal to the axis of the mandrel to permit joining at points which are laterally displaced from each other on the substantially flat surface.

13. Apparatus for fabricating a stent, comprising:
a) a platform adapted to receive a sheet of material to be formed into the stent, the sheet having a longitudinal axis, a first major surface, a second major surface, a first long side, and a second long side; the first long side provided with a plurality of weld points and the second long side provided with a plurality of corresponding weld points; the weld points disposed so that when the sheet is formed into a substantially tubular shape, the weld points on the first long side are adjacent to the corresponding weld points on the second long side to form a plurality of weld point pairs and the weld point pairs are not disposed along a single common weld line parallel to the longitudinal axis of the stent;
b) a mandrel having an external surface and a first end and a second end defining a longitudinal axis, the mandrel sized to have an external perimeter about the longitudinal axis substantially equal to or less than the internal perimeter of the stent to be fabricated, the external surface provided with at least one substantially flat surface extending between the first end and the second end;
c) means for deforming the sheet against the external surface of the mandrel so that the sheet is deformed into a substantially tubular shape;
d) means for aligning and securing the weld points on the first long side and the corresponding weld points on the second long side to form the plurality of weld point pairs so that the weld points comprising each weld point pair can be joined; and
e) means for joining the weld points on the first long side to the corresponding weld points on the second long side, the means for deforming and the means for aligning and securing adapted to secure the aligned weld points comprising the weld point pairs adjacent to the substantially flat surface of the mandrel so that the aligned weld points lie in a plane that is substantially perpendicular to the application of the means for joining.

14. The apparatus of claim 13, wherein the means for joining is a welding apparatus.

15. The apparatus of claim 14, wherein the welding apparatus is a laser-welding apparatus.

16. The apparatus of claim 13, wherein the means for joining is a gluing apparatus.

17. Apparatus for fabricating a stent, comprising:
a) a platform adapted to receive a sheet of material to be formed into the stent, the sheet having a longitudinal axis, a first major surface, a second major surface, a first long side, and a second long side; the first long side provided with a plurality of weld points and the second long side provided with a plurality of corresponding weld points; the weld points disposed so that when the sheet is formed into a substantially tubular shape, the weld points on the first long side are adjacent to the corresponding weld points on the second long side to form a plurality of weld point pairs disposed on a plurality of weld lines;
b) a mandrel having an external surface and a first end and a second end defining a longitudinal axis, the mandrel sized to have an external perimeter about the longitudinal axis substantially equal to or less than the internal perimeter of the stent to be fabricated, the external surface provided with at least one substantially flat surface extending between the first end and the second end;
c) means for deforming the sheet against the external surface of the mandrel so that the sheet is deformed into a substantially tubular shape;
d) means for aligning and securing the weld points on the first long side and the corresponding weld points on the second long side to form a plurality of weld point pairs so that the corresponding weld points comprising the weld point pairs can be joined; and e) means for joining the weld points on the first long side to the corresponding second weld points on the second long side, the means for deforming and the means for aligning and securing adapted to secure the aligned weld points adjacent to the substantially flat surface of the mandrel so that each of the aligned weld points comprising each of the weld point pairs disposed on each of the plurality of weld lines lies in a plane that is substantially perpendicular to the application of the means for joining.

18. The apparatus of claim 17, wherein the means for joining is a welding apparatus.

19. The apparatus of claim 18, wherein the welding apparatus is a laser-welding apparatus.

20. The apparatus of claim 17, wherein the means for joining is a gluing apparatus.

21. Apparatus for fabricating a stent, comprising:

a) a platform adapted to receive a sheet of material to be formed into the stent, the sheet of material having a longitudinal axis, a first major surface, a second major surface, a first long side, and a second long side, the first and second long sides substantially parallel to the longitudinal axis of the sheet; the first long side provided with a plurality of first weld line weld points and a plurality of second weld line weld points and the second long side provided with a plurality of first weld line weld points and a plurality of second weld line weld points;

the weld points disposed so that when the sheet is formed into a substantially tubular shape the first weld line weld points on the first long side are adjacent to the corresponding first weld line weld points on the second long side to form a plurality of first weld line weld point pairs disposed on a first weld line having a longitudinal axis substantially parallel to the longitudinal axis of the sheet;

the weld points disposed so that when the stent is formed into a substantially tubular shape the second weld line weld points on the first long side are adjacent to the corresponding second weld line weld points on the second long side to form a plurality of second weld line weld point pairs disposed on a second weld line having a longitudinal axis that is substantially parallel to the longitudinal axis of sheet;

b) a mandrel having an external surface and a first end and a second end defining a longitudinal axis, the external surface provided with at least one substantially flat surface extending between the first end and the second end;

c) means for deforming the sheet against the external surface of the mandrel so that the sheet is deformed into a substantially tubular shape, the means for deforming adapted so that the first long side and the second long side remain substantially parallel to each other when the sheet is deformed into the tubular shape;

d) means for aligning and securing the first weld line weld points on the first long side to the corresponding first weld line weld points on the second long side and for aligning and securing the second weld line weld points on the first long side to the corresponding second weld line weld points on the second long side so that the weld points comprising each weld point pair can be connected; and e) means for joining the aligned first weld line weld points of the first weld line and the aligned second weld line weld points of the second weld line, the means for deforming and the means for aligning and securing adapted to secure the aligned first weld points and the aligned second weld points adjacent to the substantially flat surface of the mandrel so that the aligned weld points of each weld point pair disposed on the first and second weld lines lie in a plane that is substantially perpendicular to the application of the means for joining.

22. The apparatus of claim 21, wherein the means for joining is a welding apparatus.

23. The apparatus of claim 22, wherein the welding apparatus is a laser-welding apparatus.

24. The apparatus of claim 21, wherein the means for joining is a gluing apparatus.

25. The apparatus of any of claim 1, 6, 6, 8, 13, 17, or 21, wherein the substantially flat surface of the mandrel is provided with at least one void.

26. The apparatus of any of claim 1, 6, 6, 8, 13, 17, or 21, wherein the substantially flat surface of the mandrel is provided with at least one groove having a longitudinal axis.

27. The apparatus of claim 26, wherein the longitudinal axis of the groove is substantially parallel to the longitudinal axis of the mandrel.

28. The apparatus of claim 8, 13, 17, or 21, wherein the sheet is comprised of a material selected from the group consisting of metals and plastics.

29. The apparatus of claim 28, wherein the metal is selected from the group consisting of stainless steel and nickel-titanium alloys.

30. The apparatus of claim 13, 17, or 21, wherein the means for deforming and the means for aligning and securing are further adapted to provide a substantially v-shaped notch between the weld points when the weld points are aligned and secured adjacent to the substantially flat surface of the mandrel.

31. The apparatus of claim 13, 17, or 21, wherein the first and second long sides of the flat sheet are substantially parallel to the longitudinal axis of the sheet.

32. The apparatus of claim 31, wherein the means for deforming is adapted so that the first long side and the second long side remain substantially parallel to each other when the sheet is deformed into the tubular shape.

33. The apparatus of claim 9, 14, 18, or 22, wherein the welding apparatus is selected from the group consisting of spot welders and arc welders.

34. A method comprising:

a) wrapping a sheet provided with a stent pattern and having two opposed sides about a mandrel having an axis, and having a flat surface, so as to cause the two opposing sides to meet adjacent to the flat surface; and b) utilizing a means for joining to join the two opposing sides at least at two points lying on lines on the surface parallel to the axis, but laterally displaced from each other on the flat surface, directing the means for joining substantially perpendicular to the flat surface.

35. The method according to claim 24, comprising joining a plurality of points located on each of said lines laterally displaced from each other.

36. A method comprising:

a) wrapping a sheet provided with a stent pattern and having two opposed sides about a mandrel having an axis, and having a flat surface, so as to cause the two opposing sides to meet adjacent to the flat surface; and b) utilizing a means for joining to join the two opposing sides at least at two points that do not lie on a single line parallel to the mandrel's longitudinal axis, directing the means for joining substantially perpendicular to the flat surface.

37. The method according to claim 34 or 36, wherein the joining step comprises welding.

38. The method according to claim 37, wherein the welding step is laser welding.

39. The method of claim 34 or 36, wherein the joining step comprises gluing.

40. A method of making a stent, comprising the steps of:
   a) utilizing a sheet of material to be formed into the stent, the sheet having a longitudinal axis, a first major surface, a second major surface, a first long side, and a second long side, the first long side provided with a plurality of weld points and the second long side provided with a plurality of corresponding weld points; the weld points disposed so that when the sheet is formed into a substantially tubular shape, the weld points on the first long side are adjacent to the corresponding weld points on the second long side to form a plurality of weld point pairs and the weld point pairs are not aligned along a common weld line parallel to the longitudinal axis of the sheet;
   b) deforming the sheet against the external surface of a mandrel so that the sheet is deformed into a substantially tubular shape; the mandrel having an external surface and a first end and a second end defining a longitudinal axis, the mandrel sized to have an external perimeter about the longitudinal axis substantially equal to or less than the internal perimeter of the stent to be fabricated, the external surface provided with at least one substantially flat surface extending between the first end and the second end;
   c) aligning and securing adjacent the substantially flat surface of the mandrel each of the weld points so that the weld points lie in substantially the same plane that is substantially parallel to the substantially flat surface of the mandrel, and so that the weld points on the first long side are adjacent to the corresponding weld points on the second long side to form a plurality of weld point pairs that are not disposed only along a single common weld line; and
   d) joining the corresponding weld points comprising each weld point pair utilizing a means for joining, the means for joining directed substantially perpendicular to the plane in which the weld points lie.

41. The method of claim 40, wherein the joining step comprises welding.

42. The method of claim 41, wherein the welding step is laser welding.

43. The method of claim 40, wherein the joining step comprises gluing.

44. A method of making a stent, comprising the steps of:
   a) utilizing a sheet of material to be formed into the stent, the sheet having a longitudinal axis, a first major surface, a second major surface, a first long side, and a second long side, the first long side provided with a plurality of weld points and the second long side provided with a plurality of corresponding weld points; the weld points disposed so that when the stent is formed into a substantially tubular shape, the weld points on the first long side are adjacent to the corresponding weld points on the second long side to form a plurality of weld point pairs disposed on a plurality of weld lines;
   b) deforming the sheet against the external surface of a mandrel so that the sheet is deformed into a substantially tubular shape; the mandrel having an external surface and a first end and a second end defining a longitudinal axis, the mandrel sized to have an external perimeter about the longitudinal axis substantially equal to or less than the internal perimeter of the stent to be fabricated, the external surface provided with at least one substantially flat surface extending between the first end and the second end;
   c) aligning and securing adjacent to the substantially flat surface of the mandrel each of the plurality of weld points to form a plurality of weld point pairs disposed along each of the plurality of weld lines so that the weld points disposed on each of the plurality of weld lines lies in substantially the same plane that is substantially parallel to the substantially flat surface of the mandrel, and so that the weld points on the first long side are adjacent to the corresponding weld points on the second long side to form a plurality of weld point pairs disposed on a plurality of weld lines; and
   d) joining the corresponding weld points comprising each weld point pair disposed on the plurality of weld lines utilizing a means for joining, the means for joining directed substantially perpendicular to the plane in which the weld points lie.

45. The method of claim 44, wherein the joining step comprises welding.

46. The method of claim 45, wherein the welding step is laser welding.

47. The method of claim 44, wherein the joining step comprises gluing.

48. A method of making a stent, comprising the steps of:
   a) utilizing a sheet of material to be formed into the stent, the sheet having a longitudinal axis, a first major surface, a second major surface, a first long side, and a second long side, the first and second long sides substantially parallel to the longitudinal axis of the sheet; the first long side provided with a plurality of first weld line weld points and a plurality of second weld line weld points and the second long side provided with a plurality of first weld line weld points and a plurality of second weld line weld points; the weld points disposed so that when the sheet is formed into a substantially tubular shape, the first weld line weld points on the first long side are adjacent to the corresponding first weld line weld points on the second long side to form a plurality of first weld line weld point pairs disposed on a first weld line having a longitudinal axis substantially parallel to the longitudinal axis of the sheet; the weld points disposed so that when the stent is formed into a substantially tubular shape the second weld line weld points on the first long side are adjacent to the corresponding second weld line weld points on the second long side to form a plurality of second weld line weld point pairs disposed on a second weld line having a longitudinal axis that is substantially parallel to the longitudinal axis of the sheet;
   b) deforming the sheet against the external surface of a mandrel so that the sheet is deformed into a substantially tubular shape; the mandrel having an external surface and a first end and a second end defining a longitudinal axis, the mandrel sized to have an external perimeter about the longitudinal axis substantially equal to or less than the internal perimeter of the stent to be fabricated, the external surface provided with at least one substantially flat surface extending between the first end and the second end;
   c) aligning and securing adjacent to the substantially flat surface of the mandrel the first and second weld points so that so that the first weld line weld points on the first long side are adjacent to the corresponding first weld line weld points on the second long side to form a plurality of first weld line weld point pairs disposed on a first weld line having a longitudinal axis substantially parallel to the longitudinal axis of the sheet; and so that the second weld line weld points on the first long side are adjacent to the corresponding second weld line weld points on the second long side to form a plurality of second weld line weld point pairs disposed on a second weld line having a longitudinal axis that is substantially parallel to the longitudinal axis of the sheet; and so that the first and second weld points comprising the weld point pairs disposed on the first and second weld lines lie in substantially the same plane that is substantially parallel to the substantially flat surface of the mandrel; and d) joining the first weld points comprising each of the first weld point pairs disposed on the first weld line and connecting the second weld points comprising each of the second weld point pairs disposed on the second weld line utilizing a means for joining, the means for joining directed substantially perpendicular to the plane in which the first and second weld points lie.

49. The method of claim 48, wherein the joining step comprises welding.

50. The method of claim 49, wherein the welding step is laser welding.

51. The method of claim 48, wherein the joining step comprises gluing.

52. The method of claim 40, 44, or 48, further comprising the step of providing a substantially v-shaped notch between the weld points prior to carrying out step d).

53. The method of claim 52, wherein the v-shaped notch is provided during step c).

54. The method of claim 34, 36, 40, 44, or 48, further comprising the step of providing the sheet with first and second long sides that are substantially parallel to the longitudinal axis of the sheet.

55. The method of claim 54, further comprising the step of aligning the first long side and the second long side so that the first long side and the second long side remain substantially parallel to each other when the sheet is deformed into the tubular shape.

56. The method of claim 34, 36, 40, 44, or 48, wherein the sheet is comprised of a material selected from the group consisting of metals and plastics.

57. The method of claim 56, wherein the metal is selected from the group consisting of stainless steel and nickel-titanium alloys.

58. The method of claim 37, 41, 45, or 49, wherein the welding step is carried out using a welding method selected from the group consisting of spot welding and arc welding.

59. A method comprising:
a) wrapping a sheet provided with a stent pattern and having two opposed sides about a mandrel having an axis, and having a flat surface, so as to cause the two opposing sides to meet adjacent to the flat surface; and
b) utilizing laser welding to join the two opposing sides at least at two points lying on lines on the surface parallel to the axis, but laterally displaced from each other on the flat surface, directing the laser beam substantially perpendicular to the flat surface.

60. A method comprising:
a) wrapping a sheet provided with a stent pattern and having two opposed sides about a mandrel having an axis, and having a flat surface, so as to cause the two opposing sides to meet adjacent to the flat surface; and
b) utilizing laser welding to join the two opposing sides at least at two points that do not lie on a single line parallel to the mandrel's longitudinal axis, directing the laser beam substantially perpendicular to the flat surface.

61. A mandrel for forming a stent, comprising:
a member having a first end, a second end and an external surface, the external surface provided with at least one substantially flat surface extending between the first end and the second end;
wherein the substantially flat surface of the mandrel is provided with one of: (a) at least one void; and (b) at least one groove having a longitudinal axis.

62. A mandrel for forming a stent, comprising:
a member having a first end and a second end and an external surface, the external surface provided with a plurality of substantially flat surfaces, each of the flat surfaces extending between the first end and the second end;
wherein the substantially flat surface of the mandrel is provided with one of: (a) at least one void; and (b) at least one groove having a longitudinal axis.

63. The mandrel of claim 61 or 62, wherein the mandrel is provided with three substantially flat surfaces.

64. A mandrel for forming a stent comprising:
a longitudinal member having a first end and second end, the longitudinal member having a substantially triangular cross-sectional shape, wherein each of the three sides defining the substantially triangular shape is a substantially flat surface that extends between the first end and the second end of the mandrel;
wherein the substantially flat surface of the mandrel is provided with one of: (a) at least one void; and (b) at least one groove having a longitudinal axis.

65. The apparatus of claim 61, 62 or 64, wherein the longitudinal axis of the groove is substantially parallel to the longitudinal axis of the mandrel.

\* \* \* \* \*

UNITED STATES PATENT AND TRADEMARK OFFICE
CERTIFICATE OF CORRECTION

| | |
|---|---|
| PATENT NO. | : 6,821,293 B2 |
| APPLICATION NO. | : 10/280729 |
| DATED | : November 23, 2004 |
| INVENTOR(S) | : Gregory Pinchasik |

It is certified that error appears in the above-identified patent and that said Letters Patent is hereby corrected as shown below:

Col. 14 Claim 25, line 1, that portion of the claim reading "claim 1, 6, 6, 8" should read --claims 1, 2, 6, 8--
Col. 14 Claim 26, line 1, that portion of the claim reading "claim 1, 6, 6, 8" should read --claims 1, 2, 6, 8--
Col. 14 Claim 35, line 1, that portion of the claim reading "claim 24" should read --claim 34--
Col. 18 Claim 62, line 7, that portion of the claim reading "substantially fiat surface" should read --substantially flat surface--
Col. 18 Claim 64, line 8, that portion of the claim reading "substantially fiat surface" should read --substantially flat surface--

Signed and Sealed this

Second Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 6,821,293 B2  Page 1 of 1
APPLICATION NO. : 10/280729
DATED : November 23, 2004
INVENTOR(S) : Gregory Pinchasik It is certified that error appears in the above-identified patent and that said Letters Patent is hereby corrected as shown below:

Col. 14 Claim 25, line 17, that portion of the claim reading "claim 1, 6, 6, 8" should read --claims 1, 2, 6, 8--
Col. 14 Claim 26, line 20, that portion of the claim reading "claim 1, 6, 6, 8" should read --claims 1, 2, 6, 8--
Col. 14 Claim 35, line 58, that portion of the claim reading "claim 24" should read --claim 34--
Col. 18 Claim 62, line 35, that portion of the claim reading "substantially fiat surface" should read --substantially flat surface--
Col. 18 Claim 64, line 47, that portion of the claim reading "substantially fiat surface" should read --substantially flat surface--

This certificate supersedes the Certificate of Correction issued June 2, 2009.

Signed and Sealed this

Twenty-third Day of June, 2009

JOHN DOLL
*Acting Director of the United States Patent and Trademark Office*